(12) United States Patent
Zhou et al.

(10) Patent No.: US 11,813,057 B2
(45) Date of Patent: Nov. 14, 2023

(54) WEARABLE BIOSENSORS AND APPLICATIONS THEREOF

(71) Applicant: UNIVERSITY OF SOUTHERN CALIFORNIA, Los Angeles, CA (US)

(72) Inventors: Chongwu Zhou, Arcadia, CA (US); Mohammed R. Amer, Los Angeles, CA (US); Ahmad N. Abbas, Jeddah (SA); Qingzhou Liu, Pasadena, CA (US); Mervat Alharbi, Riyadh (SA)

(73) Assignees: University of Southern California, Los Angeles, CA (US); The Regents of the University of California, Oakland, CA (US); University of Jeddah, Jeddah (SA)

(*) Notice: Subject to any disclaimer, the term of this patent is extended or adjusted under 35 U.S.C. 154(b) by 496 days.

(21) Appl. No.: 16/699,314

(22) Filed: Nov. 29, 2019

(65) Prior Publication Data
US 2021/0161435 A1 Jun. 3, 2021
US 2023/0060118 A9 Feb. 23, 2023

Related U.S. Application Data

(60) Provisional application No. 62/772,855, filed on Nov. 29, 2018.

(51) Int. Cl.
A61B 5/145 (2006.01)
A61B 5/1486 (2006.01)
(Continued)

(52) U.S. Cl.
CPC ........ *A61B 5/14532* (2013.01); *A61B 5/1486* (2013.01); *A61B 5/14507* (2013.01); (Continued)

(58) Field of Classification Search
CPC ............ A61B 5/14532; A61B 5/14517; A61B 5/14546; A61B 5/1477; A61B 5/1486; (Continued)

(56) References Cited

U.S. PATENT DOCUMENTS

2007/0032089 A1* 2/2007 Nuzzo ..................... H01L 29/72
257/E21.372
2008/0063566 A1* 3/2008 Matsumoto ........ G01N 27/4146
422/50

(Continued)

OTHER PUBLICATIONS

Qingzhou Liu, Yihang Liu, Fanqi Wu, Xuan Cao, Zhen Li, Mervat Alharbi, Ahmad N. Abbas, Moh R. Amer, Chongwu Zhou, "Highly Sensitive and Wearable In2O3 Nanoribbon Transistor Biosensors with Integrated On-Chip Gate for Glucose Monitoring in Body Fluids" ACS Nano 2018, 12, 1170-1178 (Year: 2018).*
(Continued)

*Primary Examiner* — Tse W Chen
*Assistant Examiner* — Alice Ling Zou
(74) *Attorney, Agent, or Firm* — Brooks Kushman P.C.

(57) ABSTRACT

Conformable and wearable sensors with integrated on-chip gate for the detection of biomolecules, chemicals, and other substrates and applications thereof are provided. Biosensor chips can be built with In2O3 nanoribbon field-effect transistors. Biosensor chips can conform to features of a human body, enabling ability for individuals to wear a biosensor.

23 Claims, 37 Drawing Sheets

(51) Int. Cl.
  *A61B 5/00* (2006.01)
  *H01L 27/12* (2006.01)
  *A61L 31/02* (2006.01)
(52) U.S. Cl.
  CPC .......... *A61B 5/14517* (2013.01); *A61B 5/681* (2013.01); *A61B 5/6821* (2013.01); *A61B 5/6833* (2013.01); *A61L 31/022* (2013.01); *H01L 27/1225* (2013.01)
(58) Field of Classification Search
  CPC ..... A61B 5/681; A61B 5/6801; A61B 5/6821; A61B 5/6833; A61B 2562/043; A61B 5/14507; A61B 2562/046; A61B 5/1468; A61B 2562/028–0285; A61B 2562/12–125; G01N 27/27; G01N 27/3271–3272; G01N 27/414; G01N 33/48; G01N 33/50; G01N 33/66; G01N 27/4145–4148; G01N 33/5438; G01N 33/54373
  See application file for complete search history.

(56) References Cited

U.S. PATENT DOCUMENTS

| | | | |
|---|---|---|---|
| 2008/0210987 A1* | 9/2008 | Bondavalli | B82Y 15/00 257/253 |
| 2010/0184104 A1* | 7/2010 | Fahmy | G01N 33/54373 435/7.92 |
| 2017/0181669 A1* | 6/2017 | Lin | A61B 5/145 |
| 2018/0070870 A1* | 3/2018 | Emaminejad | A61B 5/4266 |
| 2018/0279930 A1* | 10/2018 | Coppedè | C12Q 1/002 |
| 2019/0120788 A1* | 4/2019 | Zhou | G01N 33/5438 |

OTHER PUBLICATIONS

You Seung Rim, Sang-Hoon Bae, Huajen Chen, Jonathan L. Yang, Jaemyung Kim, Anne M. Andrews, Paul S. Weiss, Yang Yang, Hsian-Rong Tseng, "Printable Ultrathin Metal Oxide Semiconductor-Based Conformal Biosensors" ACS Nano 2015, vol. 9, No. 12, 12174-12181 (Year: 2015).*

Woo Jin Hyun, Fazel Zare Bidosky, S. Brett Walker, Jennifer A. Lewis, Lorraine F. Francis, C. Daniel Frisbie, "Printed Self-Aligned Side-Gate Organic Transistors with a Sub-5 um Gate-Channel Distance on Imprinted Plastic Substrates" Adv. Electron. Mater. 2016, 1600293 (Year: 2016).*

Abbas, A.N. et al., "Patterning, Characterization, and Chemical Sensing Application of Graphene Nanoribbon Arrays Down to 5 nm Using Helium Ion Beam Lithography," ACSNANO, 2014, v. 8, n. 2, pp. 1538-1546.

Abikshyeet, P. et al., "Glucose estimation in the salivary secretion of diabetes mellitus patients," Diabetes, Metabolic Syndrome and Obesity: Targets and Therapy, 2012, pp. 149-154.

Aroonyadei, N. et al., "Highly Scalable, Uniform and Sensitive Biosensors Based on Top-Down Indium Oxide Nanoribbons and Electronic Enzyme-Linked Immunosorbent Assay," Nano. Lett. 2015, 15, pp. 1943-1951.

Bandodkar, A.J. et al., "Non-invasive wearable electrochemical sensors: a review," Trends in Biotechnology, Jul. 2014, v. 32, n. 7, pp. 363-371.

Claussen, J.C., et al. "Nanostructuring Platinum Nanoparticles on Multilayered Graphene Petal Nanosheets for Electrochemical Biosensing," Birck and NCN Publications, Aug. 21, 2012, 9 pgs.

Gao, W. et al., "Fully integrated wearable sensor arrays for multiplexed in situ persperiation analysis," Nature, v. 529, 2016, 18 pgs.

Heller, A., Implanted Glucose Sensors for the Management of Diabetes, Annu. Rev. Biomed. Eng. 1999, pp. 153-175.

Hrapovic, S. et al., "Electrochemical Biosensing Platforms Using Platinum Nanoparticles and Carbon Nanotubes," Analytical Chemistry, v. 76, n. 4, 2004, pp. 1083-1088.

Kaltenbrunner, M. et al., "An ultra-lightweight design for imperceptible plastic electronics," Nature, v. 499, 2013, 8 pgs.

Kim, D-H. et al., "Epidermal Electronics," Science, Aug. 12, 2011, v. 333, pp. 838-843.

Kim, J., et al. "Fabrication of High-Performance Ultrathin In2O3 Film Field-effect Transisters and Biosensors Using Chemical Lift-Off—Lithography," ACSNANO, 2015, v. 9, n. 4, pp. 4572-4582.

Lee, H. et al., "Wearable/disposable sweat-based glucose monitoring device with multistage transdermal drug delivery mode," Sci. Adv. 2017, 3, pp. 1-8.

Liao, C. et al., "Flexible, Organic Electrochemical Transistors for Highly Selective Enzyme Biosensors and Used for Saliva Testing," Adv. Mater. 2015, 27, pp. 676-681.

Lin, P. et al., "Ion-Sensitive Properties of Organic Electrochemical Transistors," ACS, v. 2, n. 6, pp. 1637-1641.

Lipomi, D.J. et al., "Skin-like pressure and strain sensors based on transparent elastic films of carbon nanotubes," Nature Nanotechnology, Dec. 2011, v. 6, pp. 788-792.

Liu, Q. et al., "Highly Sensitive and Quick Detection of Acute Myocardial Infarction Biomarkers Using In2O3 Nanoribbon Biosensors Fabricated Using Shadow Masks," ACS Nano 2016, 10, pp. 10117-10125.

Makaram, P. et al., "Trends in Nanomaterial-Based Non-Invasive Diabetes Sensing Technologies," Diagnostics 2014, 4, pp. 27-46.

Mannoor, M.S. et al., "Graphene-based wireless bacteria detection on tooth enamel," Nature Communications, 2012, pp. 1-9.

McAlpine, M.C. et al., "Highly ordered nanowire arrays on plastic substrates for ultrasensitive flexible chemical sensors," nature materials, v. 6, 2007, pp. 379-384.

Moyer, J. et al., "Correlation Between Sweat Glucose and Blood Glucose in Subjects with Diabetes," Diabetes Technology & Therapeutics, v. 14, n. 5, 2012, 5 pgs.

Olarte, O. et al., "Glucose Detection in Human Sweat Using an Electronic Nose," 35th Annual International Conference of the IEEE EMBS, Osaka, Japan, 2013, 4 pgs.

Rim, Y.S. et al., "Printable Ultrathin Metal Oxide Semiconductor-Based Conformal Biosensors," ACS, v. 9, n. 12, 2015, pp. 12174-12181.

Ronkainen, N.J. et al., "Electrochemical Biosensors," Chem. Soc. Rev. 2010, 39, pp. 1747-1763.

Someya, T. et al., "Conformable, frexible, large-area networks of pressure and thermal sensors with organic transistor active matrixes," PNAS, 2005, v. 102, n. 35, pp. 12321-12325.

Takei, K. et al., "Nanowire active-matrix circuitry for low-voltage macroscale artificial skin," Nature Materials, v. 9, 2010, pp. 821-826.

Tang, H. et al., "Highly Sensitive Glucose Biosensors Based on Organic Electrochemical Transistors Using Platinum Gate Electrodes Modified with Enzyme and Nanomaterials," Adv. Funct. Mater. 2011, 21 pp. 2264-2272.

Tang, T. et al., "Synthesis and characterization of single-crystal indium nitride nanowires," J. Mater. Res., v. 19, n. 2, 2004, pp. 423-426.

Tierney, M.J. et al., "Electroanalysis of Glucose in Transcutaneously Extracted Samples," Electroanalysis 2000, v. 12, n 9, pp. 666-671.

Vashist, S.K., "Non-invasive glucose monitoring technology in diabetes management: A review," Analytica Chimica Acta 750 (2012), pp. 16-27.

Veiseh, O. et al., "Managing diabetes with nanomedicine: challenges and opportunities," Nature Reviews, v. 14, 2015, pp. 45-57.

Wang, J. et al., "Solubilization of Carbon Nanotubes by Nafion Toward the Preparation of Amperometric Biosensors," J. Am. Chem. Soc. 2003, 125, pp. 2408-2409.

Xu, S. et al., "Soft Microfluidic Assemblies of ensors, Circuits, and Radios for the Skin," Science, 2014, v. 344, pp. 70-74.

Yan, Q. et al., "Measurement of Tear Glucose Levels with Amperometric Glucose Biosensor/Capillary Tube Configuration," Anal. Chem. 2011, 83, pp. 8341-8346.

Kao, H., et al., "A contact lens with embedded sensor for monitoring tear glucose level," Biosensors and Bioelectronics 26 (2011) pp. 3290-3296.

(56) References Cited

OTHER PUBLICATIONS

Yao, H., et al., "A contact lens with integrated telecommunication circuit and sensors for wireless and continuous tear glucose level," J. Micromech. Microeng. 2012, 10 pp.

Zhai, D. et al, "Highly Sensitive Glucose Sensor Based on PT Nanoparticle/Polyaniline Hydrogel Heterostructures," ACSNANO, 2013, v. 7, n. 4, pp. 3540-3546.

Zhang, M. et al., "Highly sensitive glucose sensors based on enzyme-modified whole-graphene solution-gated transistors," Scientific Reports, 2015, pp. 1-6.

Zhang, W. et al., "Noninvasive glucose monitoring using saliva nano-biosensor," Sensing and Bio-Sensing Research 4, 2015, pp. 23-29.

Zhang, W. et al., "On-chip highly sensitive saliva glucose sensing using multilayer films composed of single-walled carbon nanotubes, gold nanoparticles, and glucose oxidase," Sensing and Bio-Sensing Research 4, 2015, pp. 96-102.

Berman, E.R., Biochemistry of the Eye, Springer Science & Business Media (2013), selected pages: title page and pp. 69-70.

* cited by examiner

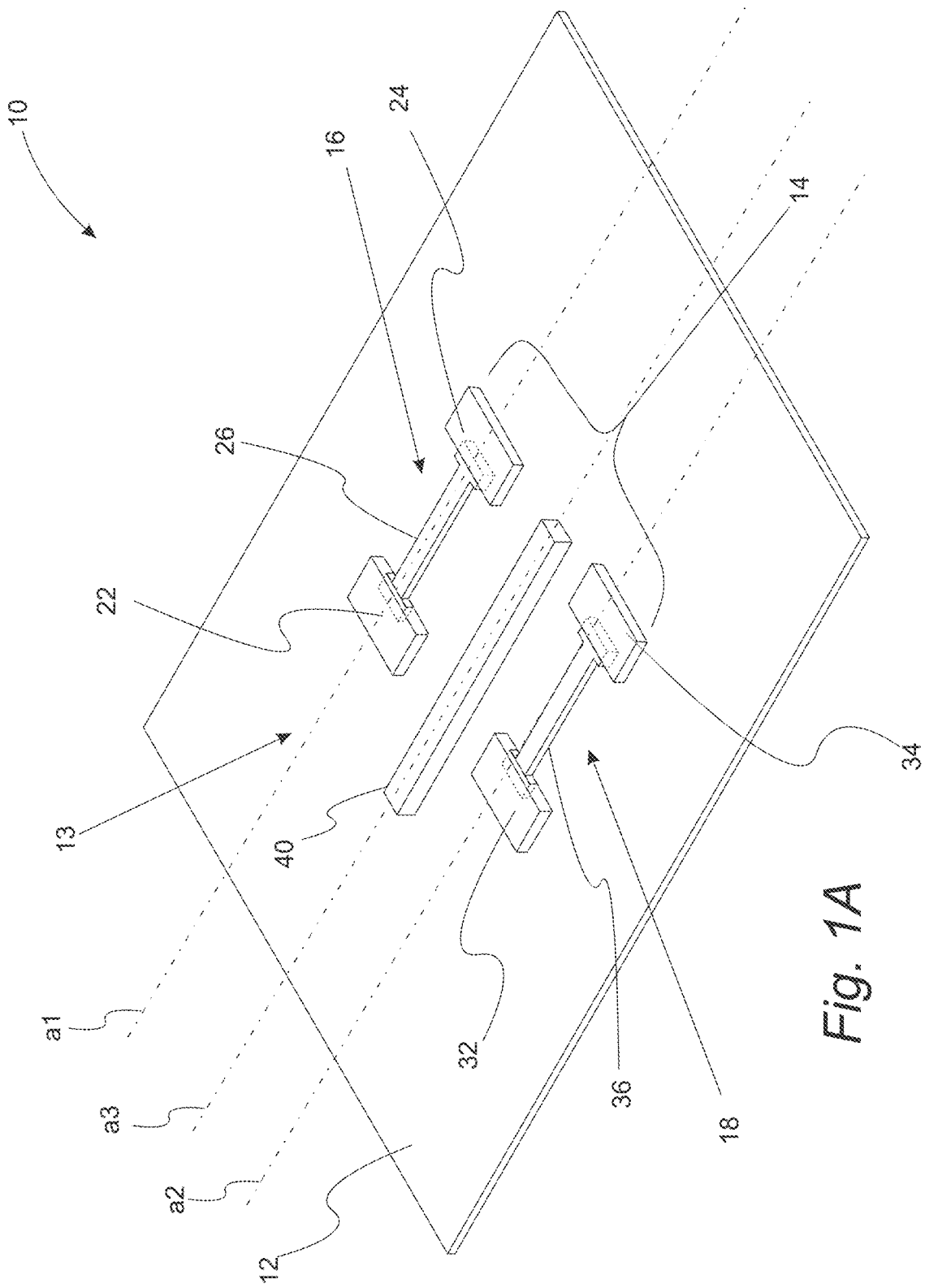

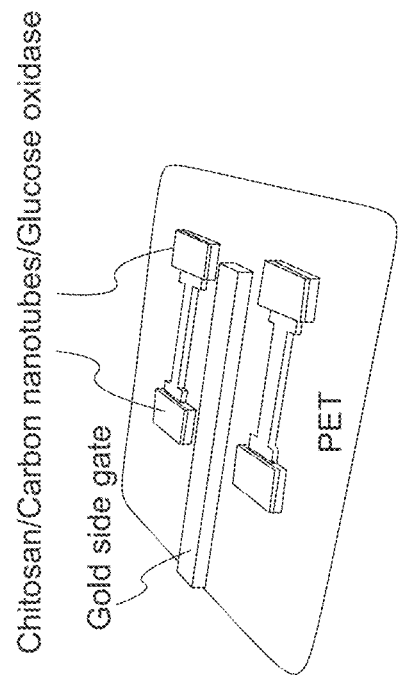
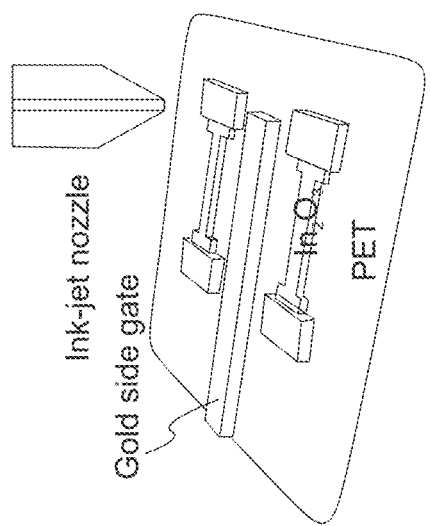
Fig. 2B

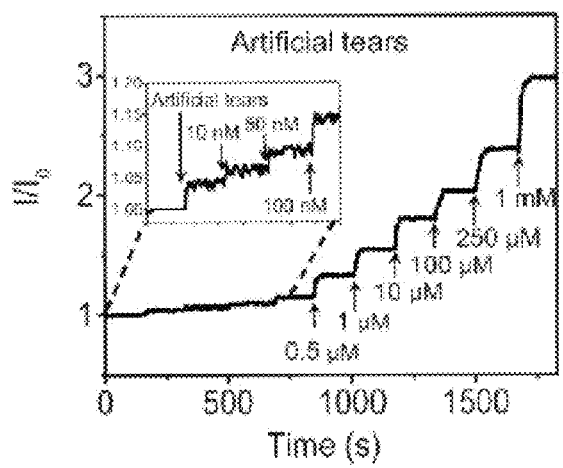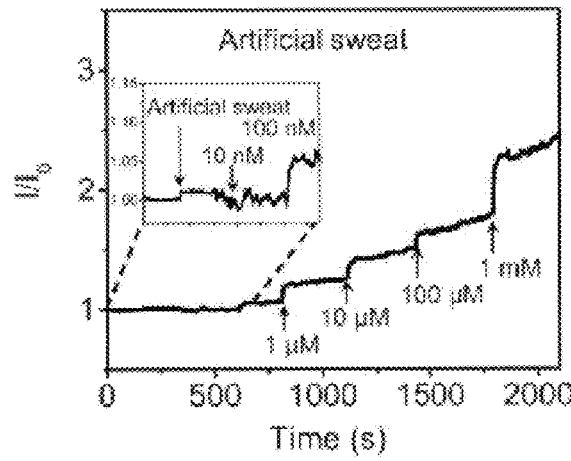
*Fig. 20A*   *Fig. 20B*
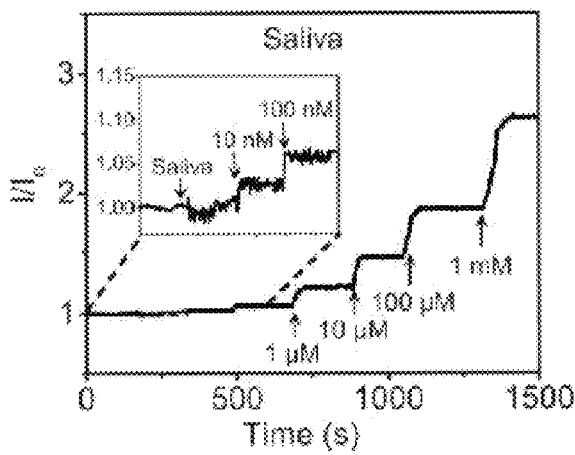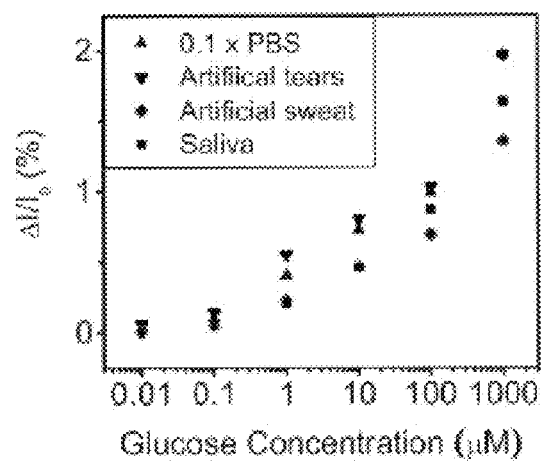
*Fig. 20C*   *Fig. 20D*

WEARABLE BIOSENSORS AND APPLICATIONS THEREOF

CROSS-REFERENCE TO RELATED APPLICATIONS

This application claims the benefit of U.S. provisional application Ser. No. 62/772,855 filed Nov. 29, 2018, the disclosure of which is hereby incorporated in its entirety by reference herein.

TECHNICAL FIELD

The invention is generally directed to biosensors, and more specifically to wearable biosensors with integrated on-chip gate electrodes.

BACKGROUND

Wearable biosensors are smart electronic devices that can be worn on the body as implant or accessories. Recent advances in microelectronics, telecommunications, and sensor manufacturing have opened up new possibilities for using wearable biosensors to continuously monitor an individual's body status without interrupting or limiting the user's motions (K. Takei, et al., Nat Mater. 2010, 9, 821; W. Gao, et al., Nature 2016, 529, 509-514; M. Kaltenbrunner, et al., Nature 2013, 499, 458-463; S. Xu, et al., Science 2014, 344, 70-74; M. McAlpine, et al., Nat. Mater. 2007, 6, 379; D. Kim, et al., Science 2011, 333, 838-843; D. J. Lipomi, et al., Nat. Nanotechnol. 2011, 6, 788-792; and H. Lee, et al., Sci. Adv. 2017, 3, e1601314; the disclosures of which are herein incorporated by reference).

Accordingly, while many commercially available wearable electronics can track users' physical activities, devices that can provide an insightful view of user's health status at molecular level need more development.

SUMMARY

Many aspects of the present invention are directed to wearable biosensors with integrated on-chip gate. More aspects are directed to highly sensitive $In_2O_3$ nanoribbon transistor biosensors capable of monitoring glucose.

Several aspects are directed to a biosensor chip that a flexible substrate. The biosensor also has at least one parallel pair of flexible extended field effect transistors deposited onto the chip substrate such that each field effect transistor has a source terminal and a drain terminal. The biosensor also has a malleable gate electrode deposited onto the chip substrate for every pair of field effect transistors such that each gate electrode is disposed halfway between and in parallel with each pair of field effect transistors. The biosensor also has a pair of malleable source electrodes deposited onto the chip substrate for every pair of field effect transistors such that the each electrode of each pair of source electrodes is in contact with a source terminal of each field effect transistors of each pair of field effect transistors. The biosensor also has a pair of drain electrodes deposited onto the chip substrate for every pair of field effect transistors such that each electrode of each pair of drain electrodes is in contact with a drain of each field effect transistors of each pair of field effect transistors.

In more aspects, the biosensor also has a glucose oxidase deposited on each source and drain electrode.

In further aspects, the biosensor also has chitosan and single-walled carbon nanotubes deposited with the glucose oxidase on each source and drain electrode.

In even more aspects, the biosensor is capable of detecting glucose in an external body fluid.

In even further aspects, the external body fluid is a fluid selected from the group consisting of sweat, tears, and saliva.

In even further more aspects, the biosensor is able to detect glucose concentrations between 10 nM to 1 mM in a solvent.

In even further more aspects, the biosensor is conformable to a human feature.

In even further more aspects, the biosensor is conformable to human skin.

In even further more aspects, the biosensor is integrated into a skin patch.

In even further more aspects, the biosensor is integrated into a watch.

In even further more aspects, the biosensor is conformable to a human eye.

In even further more aspects, the biosensor is integrated into a contact lens.

In even further more aspects, the biosensor also has a third and fourth extended field effect transistor for each pair of field effect transistors deposited onto the chip substrate such that each third and fourth field effect transistor of each pair of each field effect transistors flank their respective pair of field effect transistors, each on one outer side and situated in parallel to their respective pair of field effect transistors.

In even further more aspects, the substrate is composed of polyethylene terephthalate (PET).

In even further more aspects, the field effect transistor is composed of indium oxide ($In_2O_3$).

In even further more aspects, the gate electrode is composed of gold.

In even further more aspects, the source and drain electrodes are composed of gold.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements and wherein:

FIG. 1A is a perspective view of biosensor having at least one pair of extended field effect transistors.

FIG. 2B provides schematic diagrams of functionalization on the surface of the electrodes using ink-jet printing in accordance with various embodiments of the invention.

FIGS. 20A, 20B, 20C, and 20D provide data graphs detailing glucose sensing in artificial tears, artificial sweat, and sweat, generated in accordance with various embodiments of the invention.

DETAILED DESCRIPTION

Figure 1B:
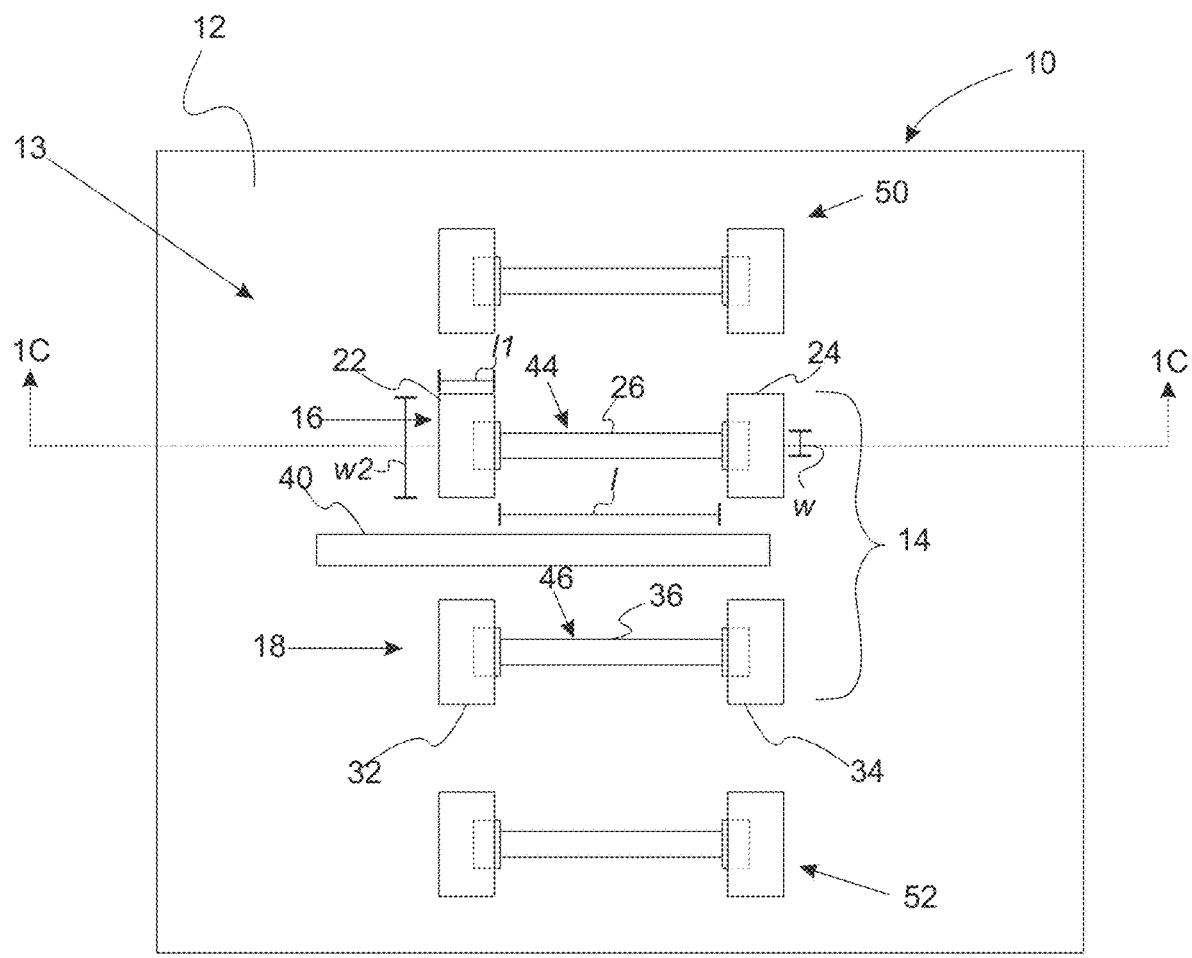
FIG. 1B is a top view of biosensor having at least one pair of extended field effect transistors.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits. In the specific examples set forth herein, concentrations, temperature, and reaction conditions (e.g. pressure, pH, etc.) can be practiced with plus or minus 50 percent of the values indicated rounded to three significant figures. In a refinement, concentrations, temperature, and reaction conditions (e.g., pressure, pH, etc.) can be practiced with plus or minus 30 percent of the values indicated rounded to three significant figures of the value provided in the examples. In another refinement, concentrations, temperature, and reaction conditions (e.g., pH, etc.) can be practiced with plus or minus 10 percent of the values indicated rounded to three significant figures of the value provided in the examples.

Throughout this application, where publications are referenced, the disclosures of these publications in their entireties are hereby incorporated by reference into this application to more fully describe the state of the art to which this invention pertains.

The prefix "nano" as used herein means that the structures described as such have at least one dimension form about 1 to 100 nm. (e.g., at least one dimension less than 100 nm).

Abbreviations:

"GO" means glucose oxidase.

"PDMS" means polydimethylsiloxane.

"PET" means polyethylene terephthalate.

In several embodiments, biosensors are capable of continuous analyte monitoring over a period time. In more embodiments, biosensors detect analytes in an external body fluid. In even more embodiments, biosensors detect analytes in sweat, tears, or saliva. In further embodiments, biosensors do not require breaking of human skin to detect an analyte. In some more embodiments, biosensors are capable of detecting and monitoring glucose levels of an individual. In even more embodiments, biosensors are capable of detection of soluble glucose concentrations between 10 nM to 1 mM.

Embodiments are also directed to flexible, conformable, and wearable body sensors that are fully integrated. Accordingly, in many embodiments, biosensors are manufactured onto a chip composed of flexible material. In some of these embodiments, the flexible material is polyethylene terephthalate (PET). In more embodiments, all electrodes and transistors are deposited directly onto a chip. In even more embodiments, the electrodes and transistors are composed of flexible materials. In some embodiments, electrodes are composed of gold. In some more embodiments, field effect transistors are composed of indium oxide ($In_2O_3$). In some particular embodiments, gold gate electrodes are deposited directly onto the chip. In several more embodiments, a biosensor is conformable to a human feature such as human skin or eye. In many further embodiments, a biosensor is integrated into a wearable device, such as a patch designed to adhere to skin, a watch, or a contact lens.

More embodiments are directed to a biosensor design. Accordingly, in several embodiments, biosensors will have a chip substrate with at least one pair or group of 4 of flexible field effect transistors (FET) deposited thereon. In many of these embodiments, each FET will have a source terminal and a drain terminal. In more embodiments, biosensors will have a chip with flexible electrodes deposited thereon. In some embodiments, biosensors will have at least one source electrode, at least one terminal electrode, and at least one gate electrode. In various embodiments, biosensors will have a gate electrode deposited on a chip halfway in between a pair of FETs deposited on said chip. In even more embodiments, biosensors will have a source electrode deposited on a chip that contacts a source terminal of a FET also deposited on said chip. In even further embodiments, biosensors will have a drain electrode deposited on a chip that contacts a drain terminal of a FET also deposited on said chip.

A common problem with classic commercial hand-held analyzers for the detection of glucose or lactate is that most of these devices require blood samples, often necessitating a finger prick or invasive sensor (e.g., needle embedded under skin) (A. J. Bandodkar and J. Wang, Trends Biotechnol., 2014, 32, 363-371, the disclosure of which is herein incorporated by reference). Accordingly, these classical detection devices are undesirable by consumers. Wearable biosensors offer a potential alternative, as they can perform continuous analyte monitoring without undesirable breaking of skin. Continuous analyte monitoring can provide great benefit, considering, for example, optimum diabetes management is best performed with regular glucose monitoring, and glucose level trends are more insightful than temporally sparse collections of data points (P. Makaram, D. Owens, and J. Aceros, Diagnostics, 2014, 4, 27-46, the disclosure of which is herein incorporated by reference). Many other medical real-time detection systems would benefit from wearable biosensors, such as, for example, detection of pathogens to alert onset of pathogenic diseases (M. S. Mannoor, Nat. Commun. 2012, 3, 763, the disclosure of which is herein incorporated by reference).

Although blood is by far the most studied and utilized sample for diagnosis, other biological fluids such as sweat, tears, and saliva, which are more readily accessible, also contain numerous biochemical analytes that can provide valuable analysis (P. Makaram, D. Owens, and J. Aceros, 2017, 2014 cited supra; and C. Liao, Adv. Mater. 2015, 27, 676-681, the disclosure of which is herein incorporated by reference). Although various recent studies suggest a diagnosis system based on the glucose concentration in external body fluids, many challenges still exist (O. Veiseh, et al., Nat. Rev. Drug Descov. 2015, 14, 45-57; O. Olarte, et al., Conf. Proc. IEEE Eng. Med. Biol. Soc. 2013, 2013, 1462-1465; and Q. Yan, et al., Anal. Chem. 2011, 83, 8341-8346; the disclosures of which are herein incorporated by reference), many challenges still exist for the accurate detection (S. K. Vashist, Anal. Chim. acta 2012, 750, 16-27; and M. Tierney, Electroanalysis 2000, 12, 666-671; the disclosures of which are herein incorporated by reference). For example, glucose concentrations in external body fluids are much lower compared with blood (J. Moyer, et al., Diabetes Technol. Ther. 2012, 14, 398-402, the disclosure of which is herein incorporated by reference). Body fluid sensing results can also be negatively affected by ambient temperature changes, mechanical deformation caused by body motion, and the sample collection procedure.

Among various types of sensors (optical, piezoelectric, and electrochemical sensors, etc.), electrochemical sensors are promising candidates for wearable technology owing to their high performance, portability, simplicity, and low cost (N. J. Ronkainen, H. B. Halsall, and W. R. Heineman, Chem. Soc. Rev. 2010, 39, 1747-1763; M. Zhang, et al., Sci. Rep., 2015, 5, 8311; D. Zhai, et al., ACS Nano. 2013, 7, 3540-3546; P. Lin, F. Yan, and H. L. Chan, ACS Appl. Mater. Interfaces 2010, 2, 1637-1641; J. C. Claussen, et al., Adv. Funct. Mater. 2012, 22, 3399-3405; and H. Tang, et al., Adv. Funct. Mater. 2011, 21, 2264-2272; the disclosures of which are herein incorporated by reference). Wearable biosensors, however, require the selection of a sensing platform with high sensitivity and reproducibility, real-time detection, and compatible integration with wearable environments (e.g., human skin, tooth, eye) (M. S. Mannoor, et al., 2012, cited supra; and A. Heller Annu. Rev. Biomed. Eng. 1999, 1, 153-175, the disclosure of which is herein incorporated by reference). Nanobiosensors based on indium oxide ($In_2O_3$) field-effect transistors (FET), in accordance with various embodiments, are well suited for wearable biosensor applications because of their quick response times enabling real-time and continuous monitoring, expansive detectable concentration range, high sensitivity, high uniformity enabling reliable sensing, and capability to integrate with microfluidic and electronic functional groups (Q. Liu, et al., ACS Nano 2016, 10, 10117-10125; N. Aroonyadet, et al., Nano Lett. 2015, 15, 1943-1951; Y. S. Rim, et al., ACS Nano 2015, 9, 12174-12181; J. Kim et al., ACS Nano 2015, 9, 4572-4582; and T. Tang, et al., J. Mater. Res. 2004, 19, 423-426; the disclosures of which are herein incorporated by reference). In further embodiments, the exposed semiconductor channel regions can be modified with various functional groups or receptors easily, and thus enable the $In_2O_3$ nanobiosensors for multiplexed sensing.

Typical FET-based biosensor platforms have individual sensors with an external Ag/AgCl solution gate electrode, which is used to set the operational point of the sensors to the optimal detection mode. The Ag/AgCl electrode is commonly used as the reference electrode in the electrochemical measurements and biosensing applications due to its ability to provide stable potential and read signals precisely. Integration of Ag/AgCl electrodes into a biosensor chip, however, remains challenging. A stand-alone fully integrated sensor array, in accordance with numerous embodiments, is better suited to build a wearable biosensor platform. Accordingly, in some embodiments, FET-based biosensors are used, wherein the gate electrode only needs to supply stable gate bias to the devices, which can be achieved by an on-chip gate electrode. The source-drain electrodes and the on-chip gate electrodes, in many embodiments, are incorporated into the straightforward 2-step shadow mask fabrication process so that no additional fabrication steps are required. In several embodiments, the integration of In2O3 glucose sensors with wearable electronics generates high impact for diabetes monitoring. In more embodiments, the development of wearable sensors for in-situ, real-time, and low-cost detection of biologically and medically important targets will generate broad impact in many applications involving electronic skin (K. Takei, et al., Nat. Mater. 2010, 9, 821-826, the disclosure of which is herein incorporated by reference), thermal regulation (T. Someya, Proc. Natl. Acad. Sci. U.S.A. 2005, 102, 12321-12325, the disclosure of which is herein incorporated by reference), chemical sensing (A. N. Abbas, et al., ACS Nano 2014, 8, 1538-1546, the disclosure of which is herein incorporated by reference), and the detection of pathogens in body fluids (M. S. Mannoor, et al., 2012, cited supra).

In a number of embodiments, highly sensitive and conformal $In_2O_3$ nanoribbon FET biosensors with fully integrated on-chip gold gate are described herein, which have been laminated onto various surfaces, such as artificial arms and watches, and have enabled glucose detection in various body fluids, such as sweat and saliva. Many devices, according to various embodiments, are fabricated through two shadow masks. In some embodiments, a first shadow mask is used to define the sputter-coating of $In_2O_3$ nanoribbons, and a second shadow mask is used for metal deposition of the source, drain and gate. In more embodiments, the source and drain electrodes are modified with the enzyme glucose oxidase (GOx), biocompatible polymer chitosan, and single-walled carbon nanotubes (SWCNT) using ink-jet printing. Gold gated $In_2O_3$ FETs, in accordance with many embodiments, provide good electrical performance on highly flexible substrates. In even more embodiments, the optimized glucose sensors deliver very wide detection ranges and high sensitivity, spanning at least 5 orders of magnitude and detection limits down to 10 nM. In some more embodiments, the non-invasive sensors are capable of glucose detection in external human body fluids, such as tears and sweat, which is demonstrated on artificial skin and eye replicas in exemplary embodiments below. Accordingly, embodiments of glucose detection platforms as described herein, are highly sensitive for glucose detections and also have many other sensing applications, including, but not limited to, detection of pathogens, chemicals, biologics, and other analytes found in body fluid.

With reference to FIGS. 1A, 1B, 1C, 1D, and 1E, schematic illustrations of a biosensor having at least one pair of extended field effect transistors are provided. Biosensor 10 includes a flexible substrate 12 and at least one field effect transistor assembly 13. In a refinement, flexible substrate 12 is composed of a plastic such as polyethylene terephthalate (PET). Sometimes, flexible substrate 12 is referred to as a "chip substrate." Biosensor 10 includes at least one pair 14 of flexible extended field effect transistors deposited onto the flexible substrate. Each pair 14 of flexible extended field effect transistors include a first electrode assembly 16 and a second electrode assembly 18. First electrode assembly 16 including a first source electrode 22, a first drain electrode 24, and a first metal oxide channel 26. First metal oxide channel 26 is disposed over and typically contacts flexible substrate 14. Mover, first metal oxide channel 26 contacts first source electrode 22 and the first drain electrode 24. Second electrode assembly 18 includes second source electrode 32, a second drain electrode 34, and a second metal oxide channel 36. Second metal oxide channel 36 is disposed over and typically contacts flexible substrate 14. Second metal oxide channel 36 contacts second source electrode 32 and second drain electrode 34. Malleable gate electrode 40 is disposed over and typically contacts flexible substrate 12. Characteristically, malleable gate electrode 40 is interposed between first electrode assembly 16 and the second electrode assembly 18. In a variation, first metal oxide channel 26 and second metal oxide channel each independently are composed of or comprise an indium oxide (e.g., $In_2O_3$). In a refinement, malleable gate electrode 40 is composed of or comprises a metal, and in particular a platinum group metal such as gold and platinum. In a further refinement, a first source electrode 22, a first drain electrode 24, second source electrode 32, and second drain electrode 34 are composed of or comprise an indium oxide (e.g., $In_2O_3$). In a refinement, malleable gate electrode 40 is composed of or comprises a metal, and in particular a platinum group metal such as gold and platinum.

Advantageously, biosensor 10 can be conformable to a human feature, and in particular, human skin. For example, biosensor 10 can be integrated into a skin patch and into a watch. When biosensor 10 is conformable to a human eye, the biosensor can be integrated into a contact lens.

In a variation, first metal oxide channel 26 includes a first ribbon section 44 having a first length and a first width where the first length being greater than the first width. Moreover, the first metal oxide channel 26 defines a first axis a1 which is a centerline through the first ribbon section. Similarly, second metal oxide channel 36 includes second ribbon section 46 having a second length and a second width where the second length being greater than the second width Second metal oxide channel 36 defines a second axis a2 which is a centerline through the second ribbon section. In a refinement, first axis a1 is substantially parallel to the second axis a2. In a further refinement, malleable gate electrode 40 has a rectangular cross-section that defines a third axis a2 through a centerline that portion of the malleable gate electrode 40 that is substantially parallel to the first axis and second axis.

In a refinement, each of first metal oxide channel 26 and second metal oxide channel 36 have a length l of 200 to 800 μm for their respective ribbon sections, a width w of 10 to 50 μm, and a thickness t of 5 to 25 nm. In further refinement, malleable gate electrode 40 has a width from 10 to 50 μm and a thickness from 5 to 100 nm. In still further refinements, first source electrode 22, first drain electrode 24, second source electrode 32, and second drain electrode 34 each independently have a length l1 from 50 to 200 μm, width w1 from 50 to 200 μm, and a thickness from 5 to 100 nm. Typically, malleable gate electrode 40 is separated from each of the ribbon sections of first metal oxide channel 26 and second metal oxide channel 36 by a distance from about 150 to 600 μm from the axis a1 or a2 to axis a3.

In another variation as depicted in FIG. 1B, biosensor 10 further includes third electrode assembly 50 and fourth electrode assembly 52 that flank pair 14 of flexible extended field effect transistors. In this regard, third electrode assembly 50 is positioned such that first electrode assembly 16 is positioned between the malleable gate electrode 40 and third electrode assembly 50. Similarly, fourth electrode assembly 52 is positioned such that second electrode assembly 18 is positioned between malleable gate electrode 40 and fourth electrode assembly 52.

Figure 1C:
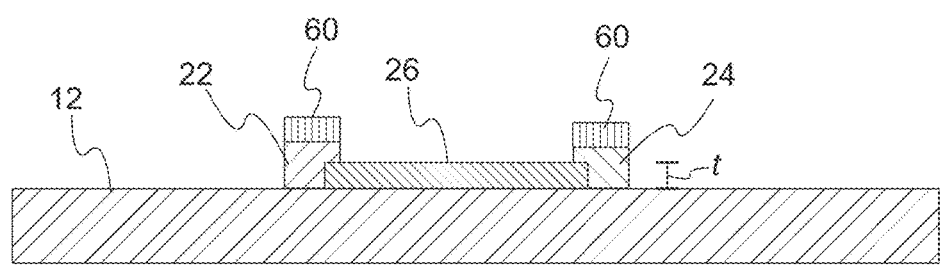
FIG. 1C is a cross sectional view of biosensor having at least one pair of extended field effect transistors.

With reference to FIG. 1C, at least one of, and typically all of, first source electrode 22, first drain electrode 24, second source electrode 32, and second drain electrode 34 can be overcoated with layers 60 including glucose oxidase.

In a refinement, first source electrode 22, first drain electrode 24, second source electrode 32, and second drain electrode 34 can be overcoated with layers 60 including chitosan and single-walled carbon nanotube. In another refinement, at least one of, and typically all of, first source electrode 22, first drain electrode 24, second source electrode 32, and second drain electrode 34 is overcoated with layers 60 of chitosan, single-walled carbon nanotube and optionally glucose oxidase. In a further refinement, biosensor 10 is capable of detecting glucose in an external body fluid (e.g., sweat, tears, and saliva). In this regard, the biosensor is able to detect glucose concentrations between 10 nM to 1 mM in a solvent.

Figure 1D:
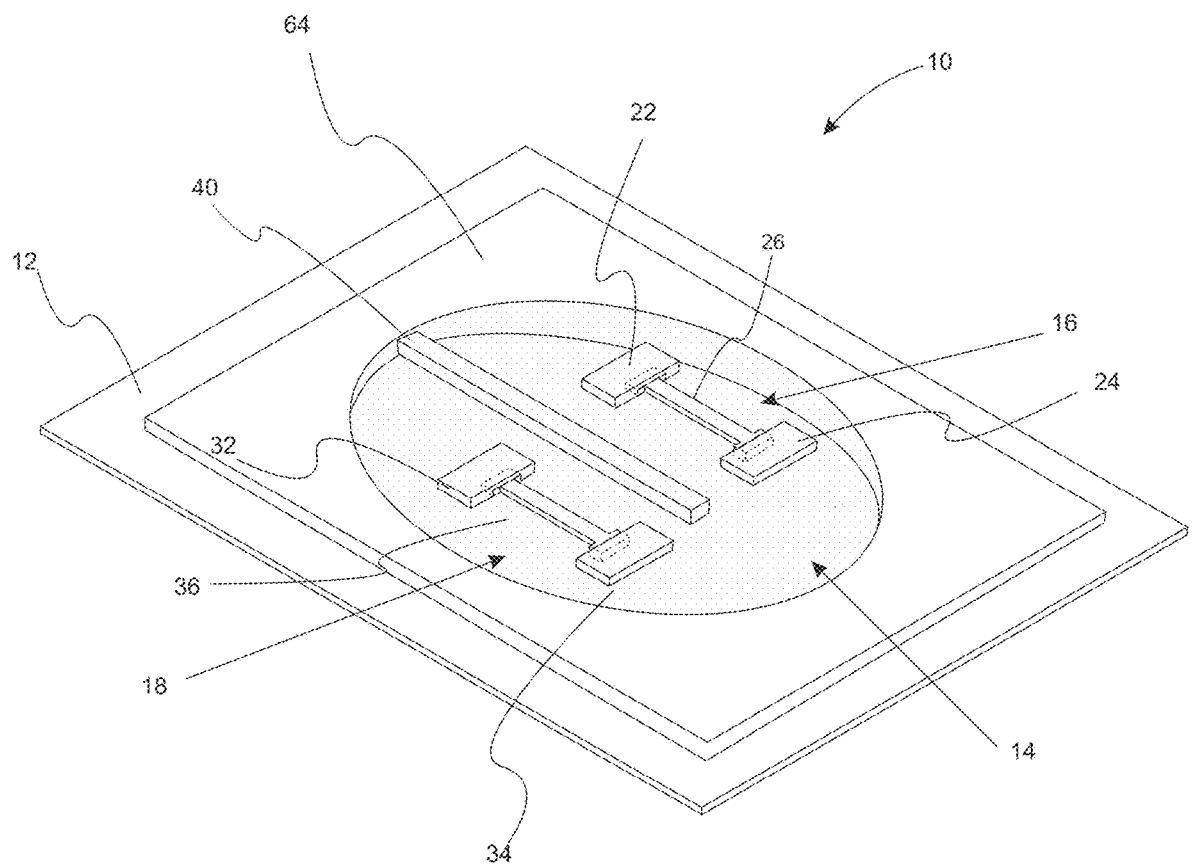
FIG. 1D is a perspective view of biosensor having at least one pair of extended field effect transistors and a microwell for collecting body fluids.
Figure 1E:
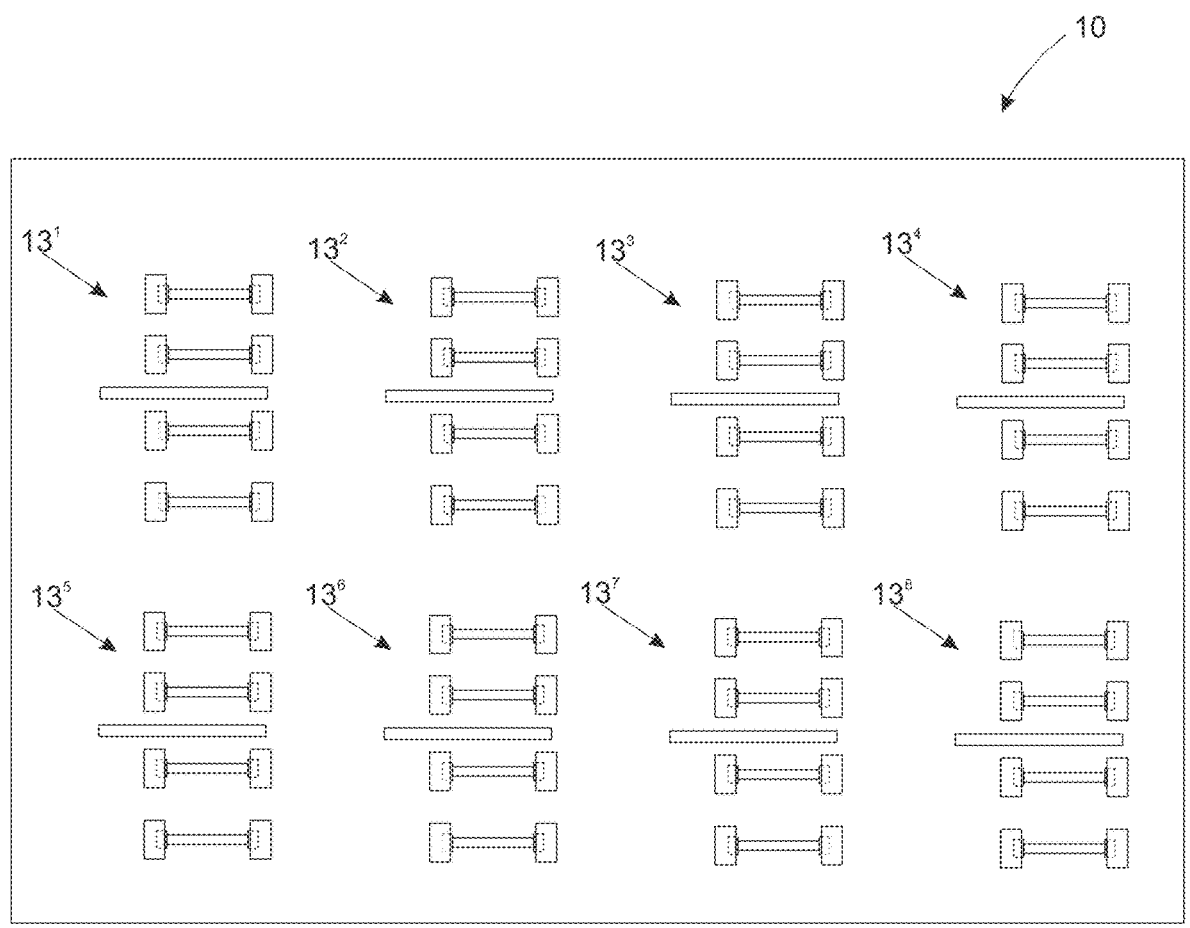
FIG. 1E is a top view of biosensor having a plurality of extended field effect transistor assemblies.

With reference to FIG. 1D, biosensor 10 can also include microwell 64 that allows collection and accumulation of body fluids. Typically, microwell 64 can also serve as a passivation layer to ensure reliable sensing without electrical disturbance that can be introduced by contacting of metal lines with a body and/or body fluids. Typically, microwell 64 can be formed from a plastic, rubber, silicone or the like. In this regard, polydimethylsiloxane is found to be particularly useful.

With reference to FIG. 1D, biosensor 10 can include one or more additional pairs of flexible of the field effect transistor assemblies 13 as set forth above. In a refinement, biosensor 10 includes from 2 to 50 of field effect transistor assemblies 13.

Figure 2A:
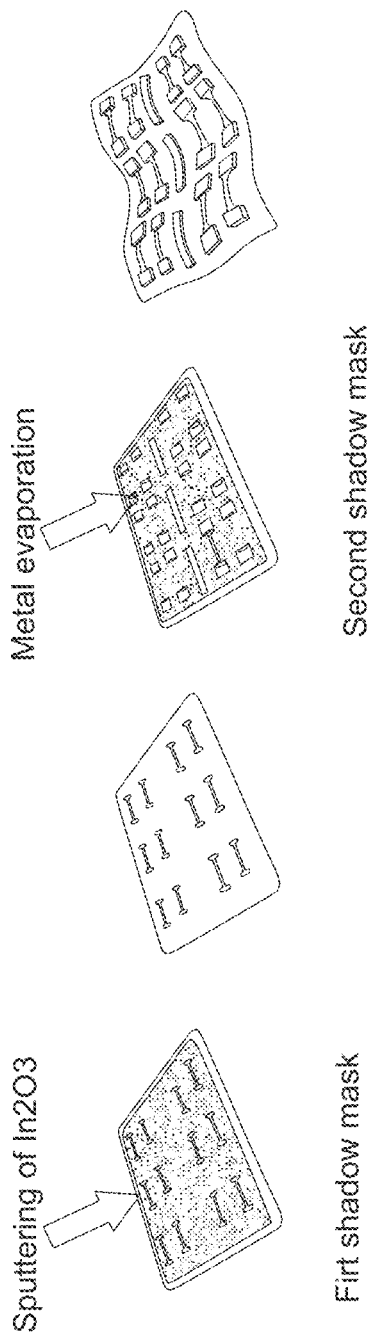
FIG. 2A provides schematic diagrams of a fabrication procedure of $In_2O_3$ FETs on a PET substrate using 2-step shadow masks in accordance with various embodiments of the invention.

In some variations, $In_2O_3$ nanoribbon devices are fabricated similarly to previously reported shadow mask fabrication technique (Q. Liu, et al, 2016, cited supra), however, side gate patterns were added to the source/drain shadow mask and also a 5 μm ultra-flexible PET substrate was used. FIG. 2B illustrates, in accordance with various embodiments, a scheme for fabricating flexible $In_2O_3$ macroelectronics on PET substrates. As shown, a PET substrate is attached to the first shadow mask using antistatic tape. Then radio frequency (RF) sputtering was used to deposit 16-nm-thick $In_2O_3$ nanoribbons through the openings on the shadow mask. The second shadow mask was then laminated onto the PET substrate to add a subsequent metal deposition. After using a single mask to define the source, drain, and gate electrodes, the as-made biosensor foil was peeled off from the shadow mask for further electrical characterization. In many previous glucose sensing studies electrochemical sensors with large working electrodes were used with drop casting functionalization (W. Gao, et al, 2016, cited supra; and H. Lee, et al., 2017, cited supra). In several embodiments, an ink-jet printing technique was developed to functionalize the constructed FET $In_2O_3$ glucose biosensors (See FIG. 2C). Due to the small dimension (~25 μm×500 μm) of the nanoribbon biosensors, utilization of the traditional drop-cast deposition method would lead the whole active sensing area to be covered by the chitosan film. In accordance with several embodiments, the channel area is to be kept exposed. Accordingly, several embodiments employ a SonoPlot printer with a 50 μm glass nozzle to print the chitosan ink only on the source and drain pads. The ink was made of chitosan, single-walled carbon nanotube and glucose oxidase, in accordance with various embodiments.

Figure 3A:
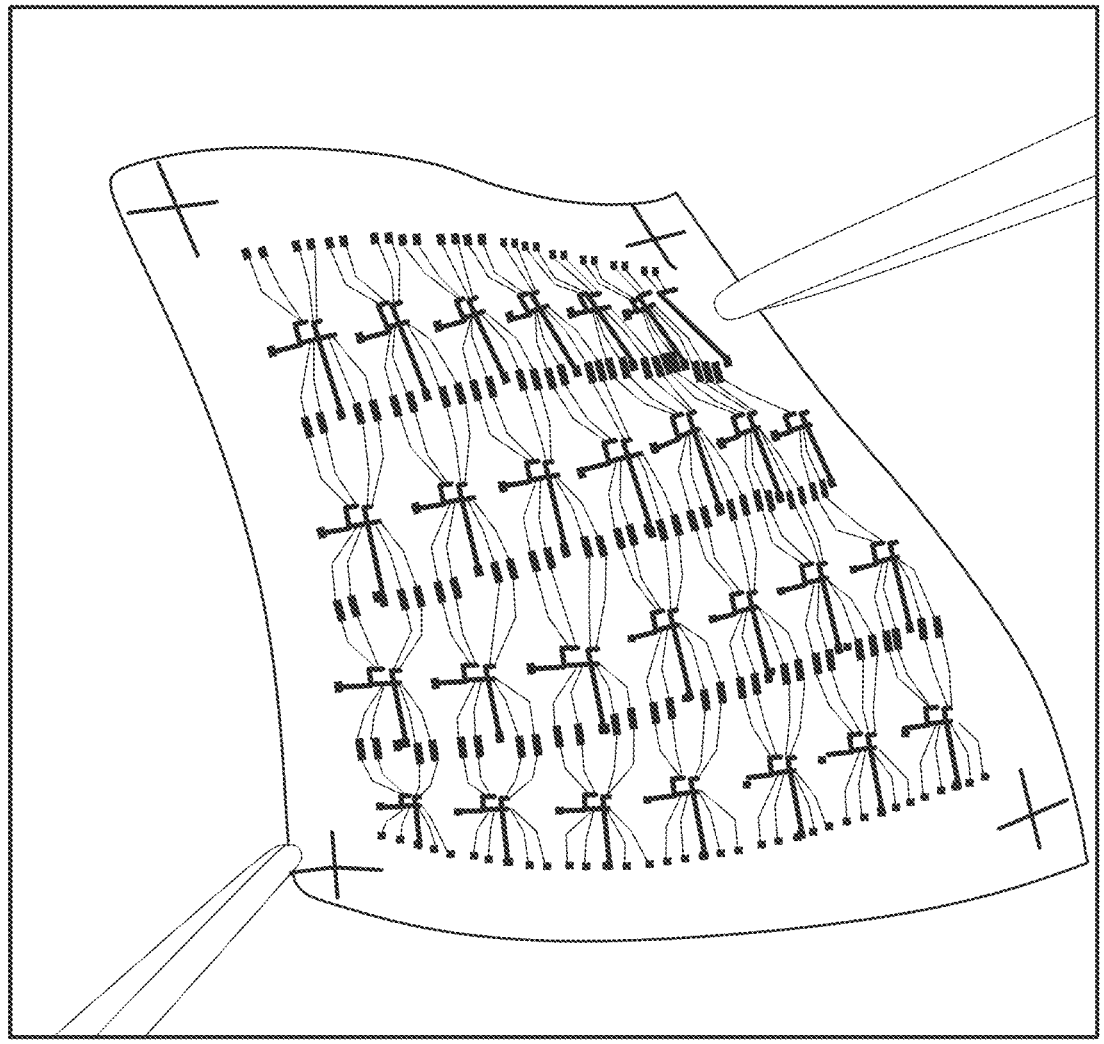
FIG. 3A provides a photograph of as-fabricated $In_2O_3$ FETs in accordance with various embodiments of the invention. Scale bar is 1 cm.
Figure 3B:
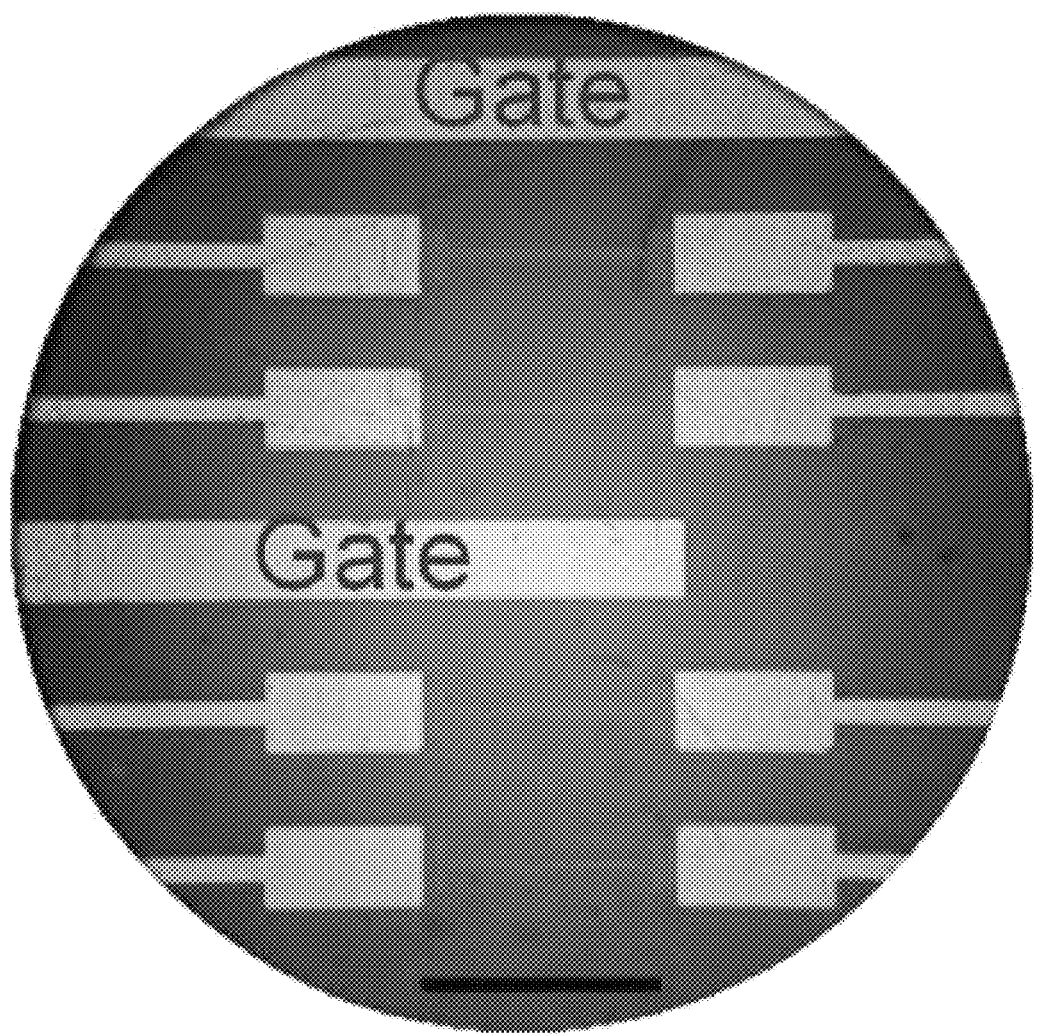
FIG. 3B provides an optical image of a group of $In_2O_3$ biosensors with two gold side gate electrodes in accordance with various embodiments of the invention. Scale bar is 500 μm.
Figure 3C:
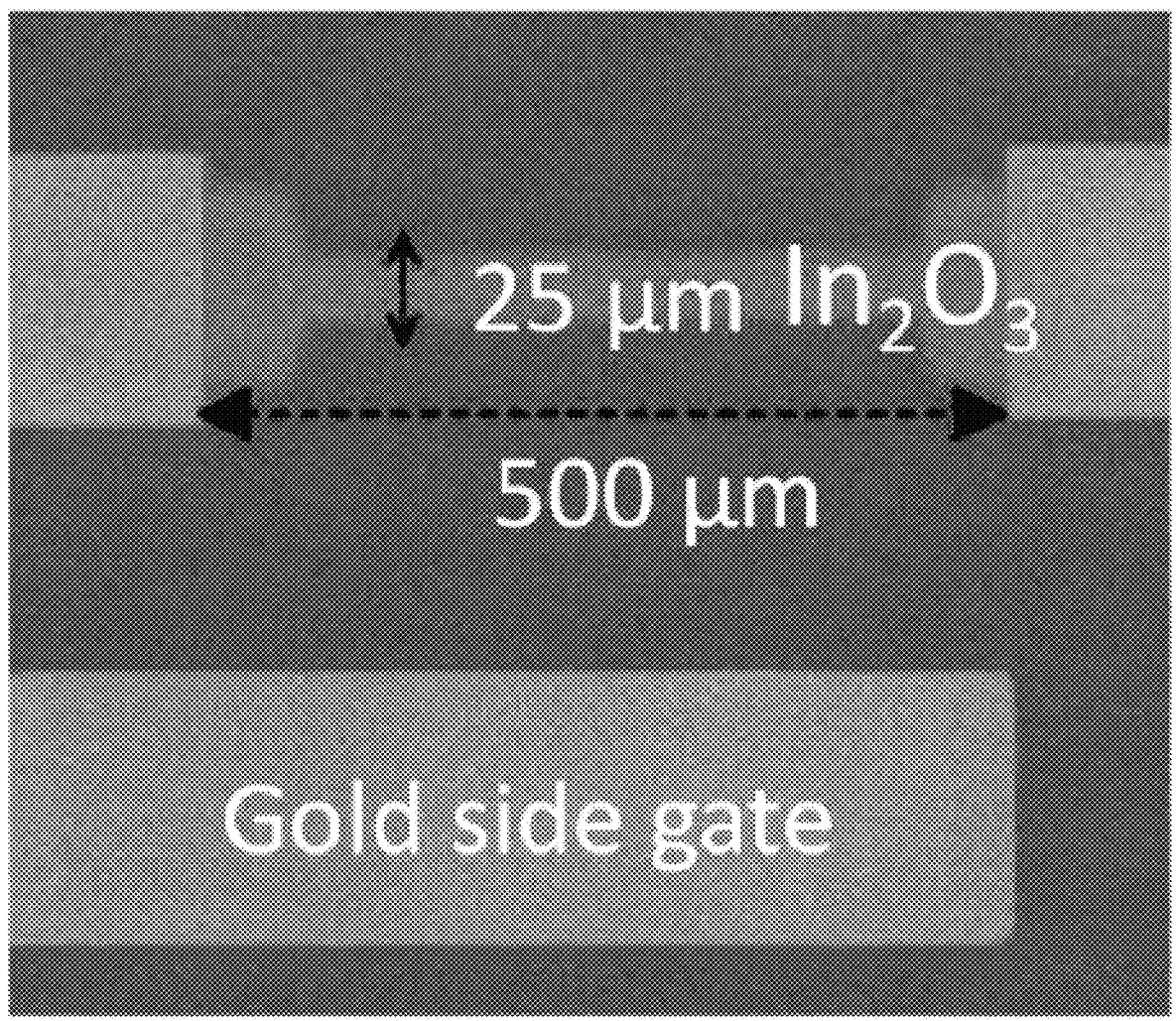
FIG. 3C provides a scanning electron microscopy image of an $In_2O_3$ nanoribbon devices (L=500 μm, W=25 μm) and a gold side gate electrode (W=150 μm) in accordance with various embodiments of the invention.
Figure 4A:
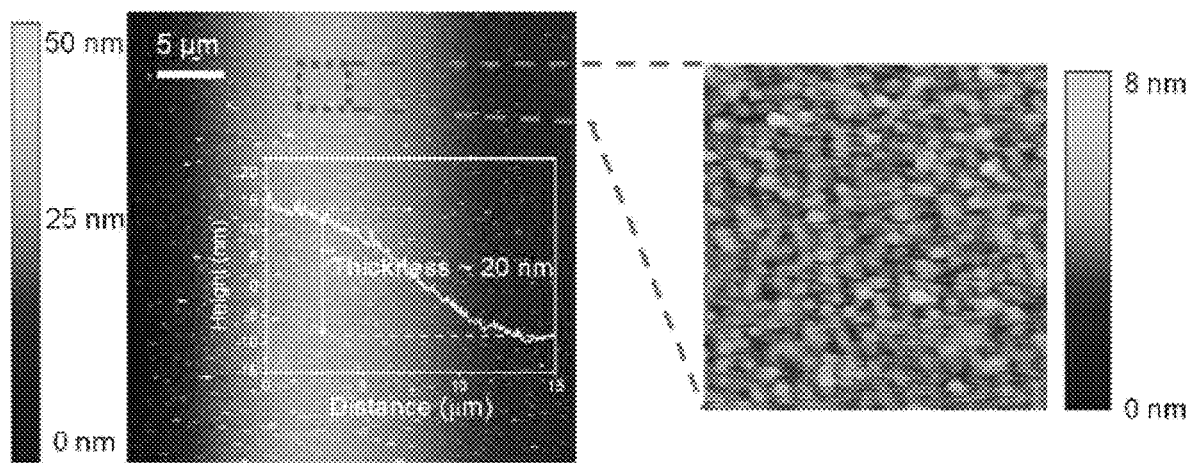
FIG. 4A provides an atomic force microscopy (AFM) image with height profile of a ~20 nm thick $In_2O_3$ nanoribbon in accordance with various embodiments of the invention.
Figure 4B:
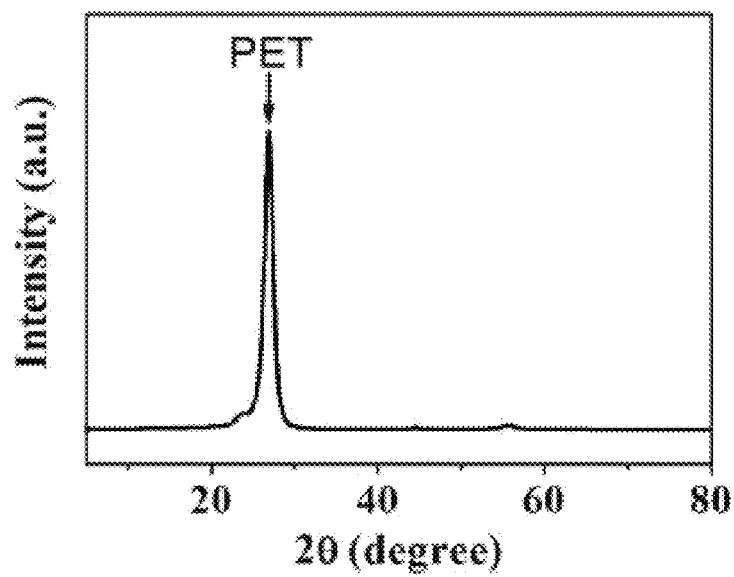
FIG. 4B provides an X-ray diffraction (XRD) of RF sputtered $In_2O_3$ film deposited on top of PET substrate in accordance with various embodiments of the invention.
Figure 5A:
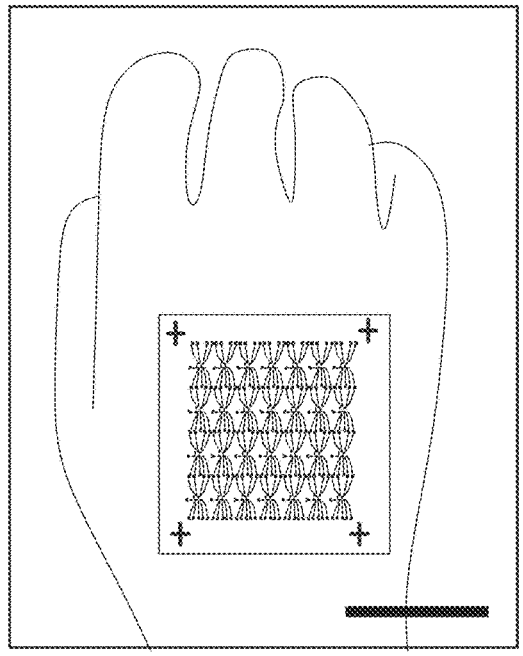
FIG. 5A provides a photograph of $In_2O_3$ FET foil laminated on an artificial human hand in accordance of various embodiments of the invention. Scale bar is 3 cm.
Figure 5B:
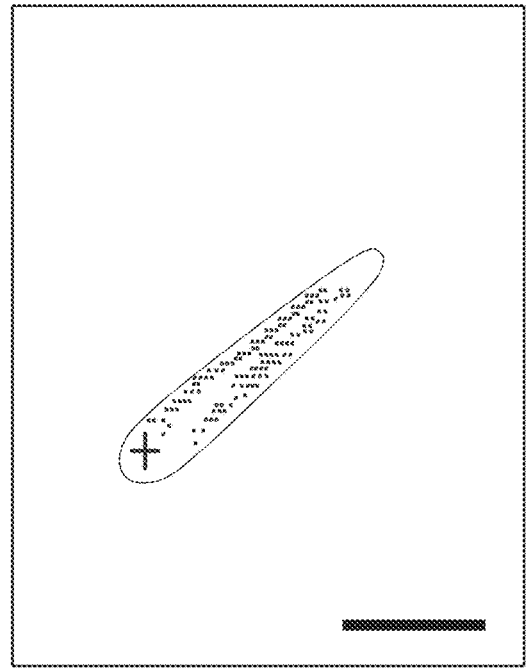
FIG. 5B provides a photograph of $In_2O_3$ biosensor foil in a rolled-up state in accordance of various embodiments of the invention. Scale bar is 3 cm.
Figure 5C:
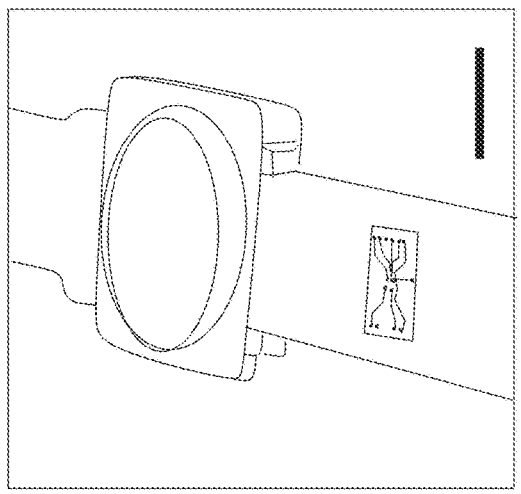
FIG. 5C provides a photograph of an $In_2O_3$ FET chip attached onto the back casing of a watch in accordance of various embodiments of the invention. Scale bar is 1 cm.

FIG. 3A provides a photograph of an embodiment of an as-fabricated $In_2O_3$ biosensor foil having a size of 5 cm×5 cm. An Optical image of a group of $In_2O_3$ biosensors and two gold gate electrodes, in accordance with more embodiments, are provided in FIG. 3B. FIG. 3C provides a scanning electron microscope (SEM) image of an embodiment displaying the channel region and the gold gate of a biosensor. To further characterize embodiments of $In_2O_3$ nanoribbons, atomic force microscopy (AFM) and X-ray diffraction (XRD) was used on samples deposited on PET substrate (FIGS. 4A and 4B). The AFM images show that the nanoribbons are solid and have clear edges. The height profile shows the thickness of $In_2O_3$ nanoribbons is ~20 nm. The XRD pattern shown presents only PET peaks, indicating the $In_2O_3$ is amorphous. FIG. 5A provides an embodiment of a fabricated $In_2O_3$ nanoribbon FET foil conformably laminated onto an artificial human hand, indicating the conformability, bendability and wearability of the $In_2O_3$ nanoribbon biosensors. FIG. 5B exhibits, in accordance with some embodiments, a biosensor foil rolled up with a radius of curvature of ~1 mm. In more embodiments, the flexible biosensor can be further attached onto the back casing of a watch (FIG. 5C), showing the concept that such $In_2O_3$ transistor biosensors can be integrated with smart watches in the future. Several more embodiments are directed to flexible, lab-on-a-chip, and conformal $In_2O_3$ nanoribbon electronics for wearable biosensor applications.

The embodiments of the invention will be better understood with the several examples provided within. Many exemplary biosensors are provided that are capable of measuring analytes, such as glucose, in bodily fluids, such as sweat, tears, and saliva. Also provided are various exemplary methods that may be utilized to practice the various embodiments. Exemplary experiments using the biosensors and methods and the resultant data are also described, further clarifying and enabling one to practice the numerous embodiments.

Electrical Characterization

Figure 6A:
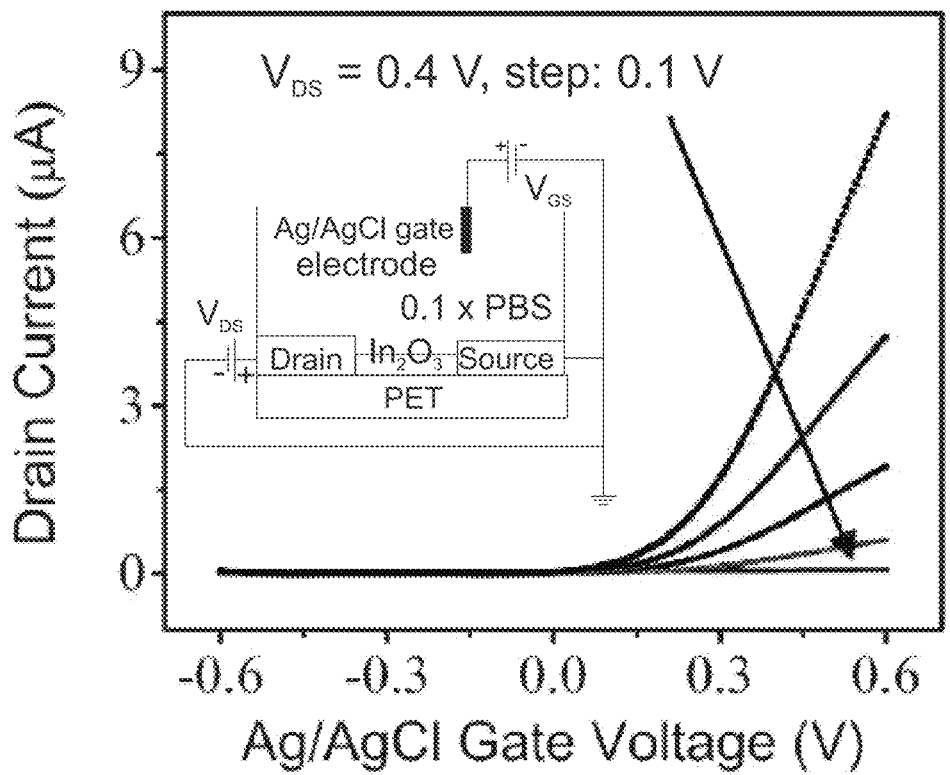
FIG. 6A provides a data plot of drain current versus Ag/AgCl gate voltage with drain voltage changing from 0.4 V to 0 V in steps of 0.1 V, generated in accordance of various embodiments of the invention. Inset shows the schematic diagram of the measurement setup.
Figure 6B:
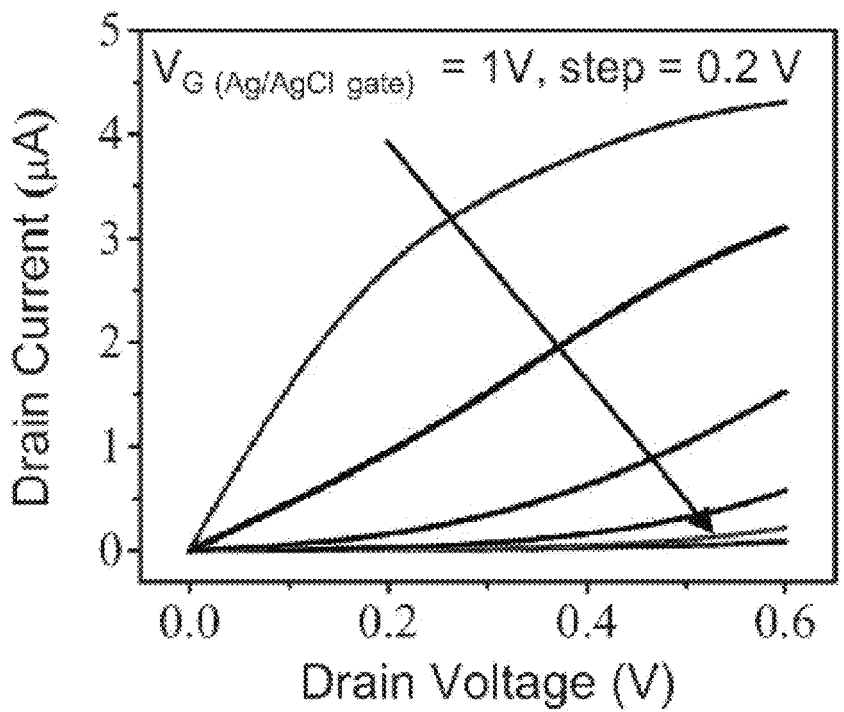
FIG. 6B provides a data plot of a family of $I_{DS}$-$V_{DS}$ curves measured with a Ag/AgCl gate electrode, generated in accordance of various embodiments of the invention.
Figure 6C:
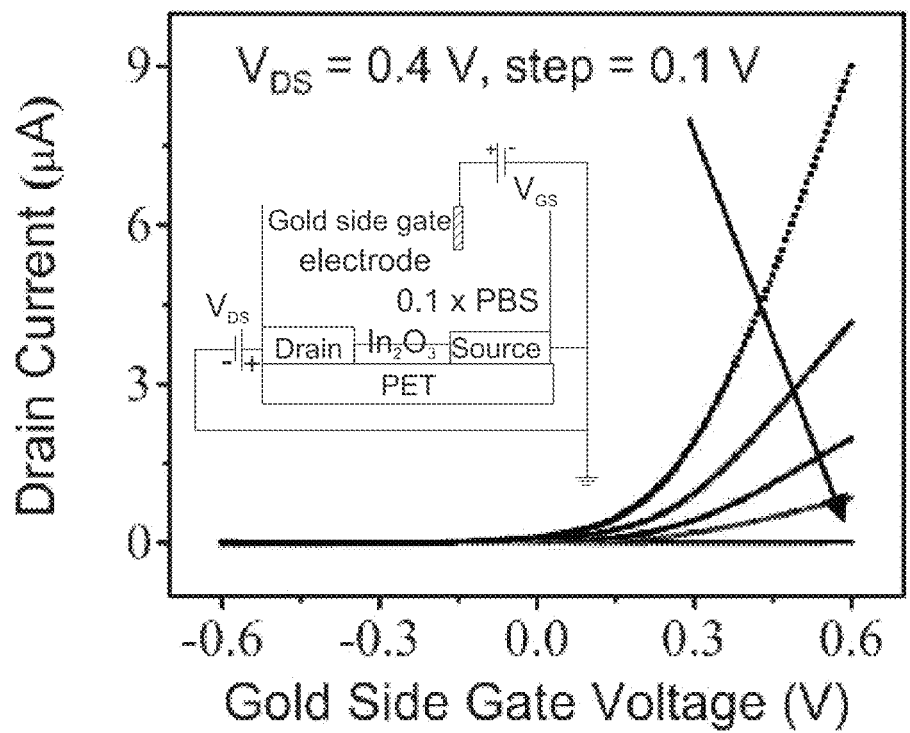
FIG. 6C provides a data plot of drain current versus gold side gate voltage with drain voltage changing from 0.4 V to 0 V in steps of 0.1 V, generated in accordance of various embodiments of the invention. Inset shows the schematic diagram of the measurement setup.
Figure 6D:
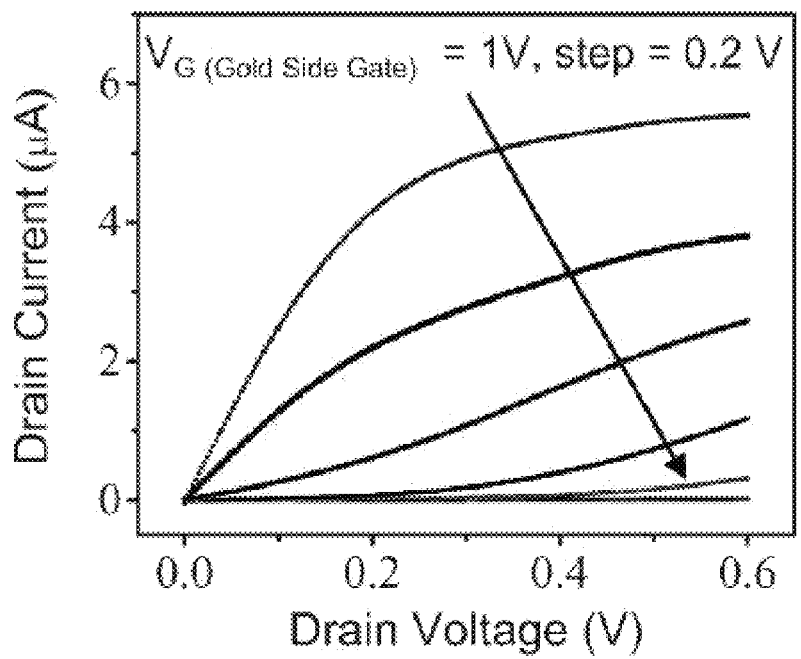
FIG. 6D provides a data plot of Family of $I_{DS}$-$V_{DS}$ curves measured with gold side gate voltage varying from 1 V to 0 V in steps of 0.2V, generated in accordance of various embodiments of the invention.
Figure 7:
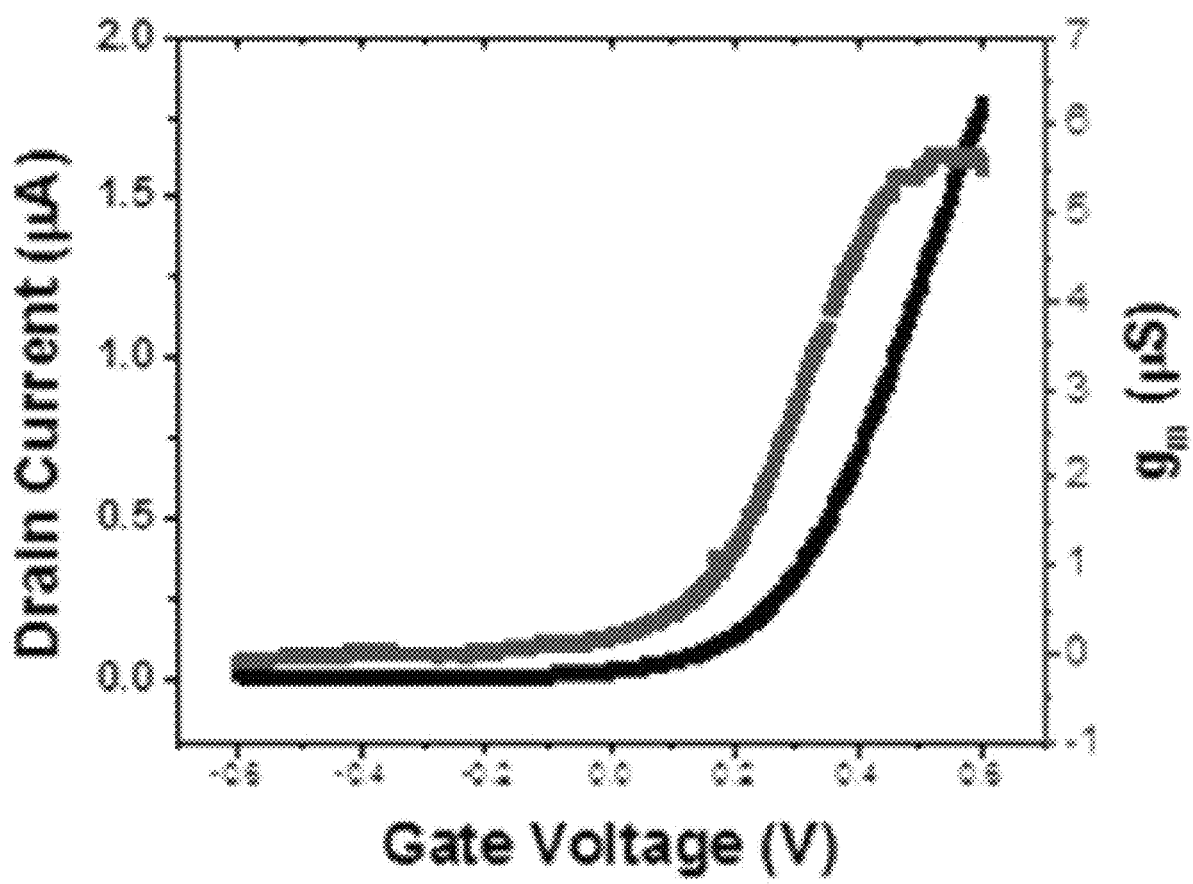
FIG. 7 provides a representative transfer curve of an $In_2O_3$ nanoribbon FET with $V_{DS}$=0.2 V and its $g_m$, generated in accordance of various embodiments of the invention.
Figure 8A:
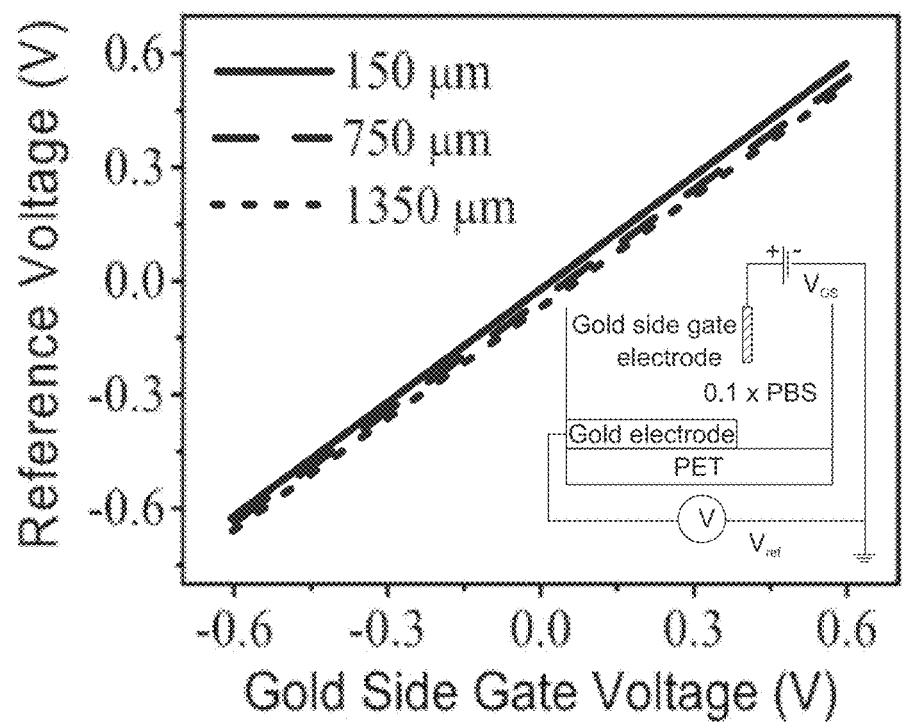
FIG. 8A provides a data plot of reference voltage measured with a gold electrode versus the gold side gate voltage, generated in accordance of various embodiments of the invention.
Figure 8B:
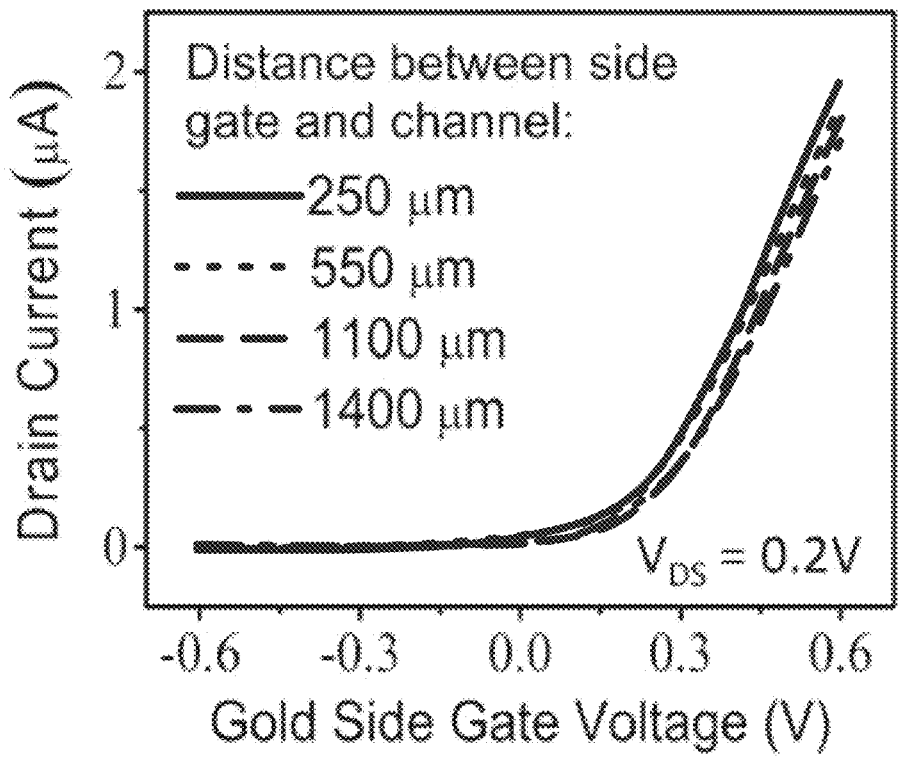
FIG. 8B provides a data plot of transfer characteristics of a representative FET with different gate-to-channel distances under $V_{DS}$=0.2 V, generated in accordance of various embodiments of the invention.
Figure 9A:
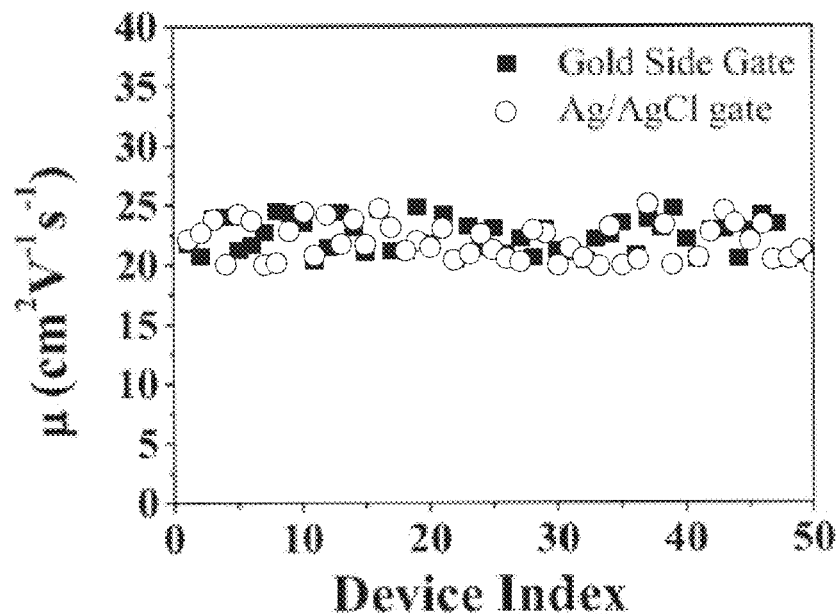
FIGS. 9A, 9B, 9C, and 9D provide data plots of electrical performances of 50 $In_2O_3$ nanoribbon transistors mobilities (μ), threshold voltage ($V_{TH}$), on/off current ratios at $V_{DS}$=0.2 V, and on-state current ($I_{ON}$) at $V_{GS}$=0.6 V and $V_{DS}$=0.2 V, generated in accordance of various embodiments of the invention.
Figure 9B:
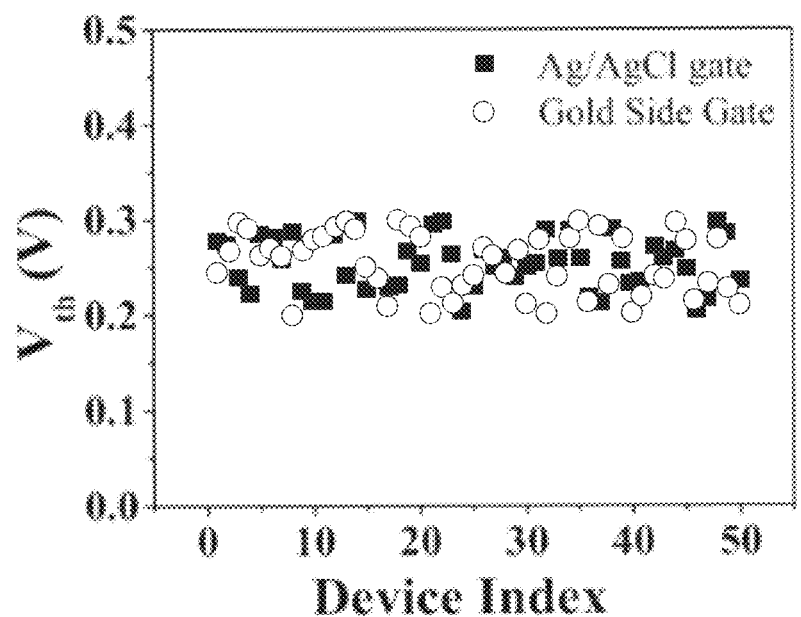
Figure 9C:
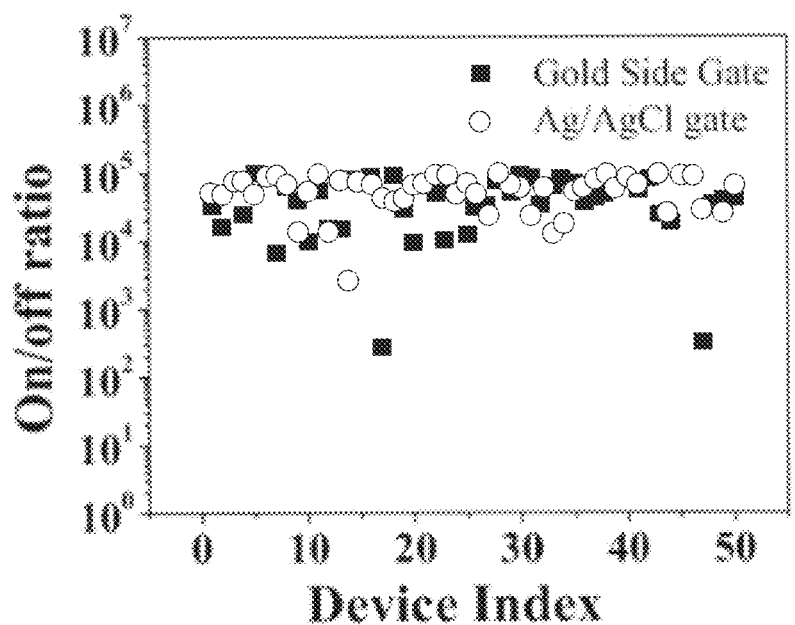
Figure 9D:
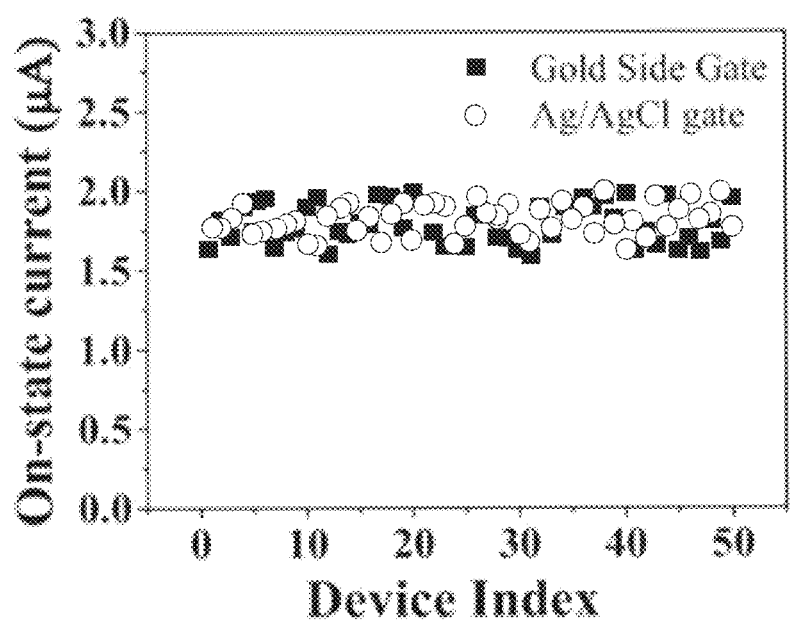

Ag/AgCl electrodes are commonly used as reference electrodes in electrochemical measurements and biosensing applications due to their ability to provide stable potential and read voltage precisely. Integration of the Ag/AgCl electrode onto a biosensor chip, however, renders fabrication difficult and impractical. In accordance with a number of embodiments, gold gates are used in lieu of Ag/AgCl external electrodes to supply gate bias to the devices. In some embodiments, two gold gate electrodes are used in a group of four $In_2O_3$ FETs. In more embodiments, gold gates are placed in the middle of the four $In_2O_3$ FETs to supply gate voltage. In even more embodiments, gold gates are placed at the rear to monitor changes in potential on the devices. Performance of devices having gate voltage applied by the external Ag/AgCl electrode or the on-chip gold electrode was compared. The measurements were performed with the device active area immersed into a microwell filled with 300 μL electrolyte solution (0.1× Phosphate Buffered Saline (PBS)). FIGS. 6A and 6B provide family curves of drain current-gate voltage ($I_{DS}$-$V_{GS}$) and drain current-drain voltage ($I_{DS}$-$V_{DS}$) when the gate voltage was biased through a Ag/AgCl electrode. The schematic diagram of the measurement setup is illustrated in the inset of FIG. 6A. The performance of gold gate controlled $In_2O_3$ FET is presented in FIGS. 6C ($I_{DS}$-$V_{GS}$) and 6D ($I_{DS}$-$V_{DS}$), generated in accordance with an embodiment of the invention. The output and transfer curves of the FET devices demonstrate that $In_2O_3$ nanoribbon devices can work properly under gate bias supplied by the gold gate. The output characteristics of the FET devices demonstrated Ohmic behavior with a good linear regime in the "on" state, and the drain current got saturated when the bias increased further. All the curves in FIGS. 6B and 6D passing through the origin point indicate the minimal contribution of the gate leakage current to the drain current. The field-effect mobility of the $In_2O_3$ FET, in accordance with various embodiments, is extracted to be 22.34±1.44 $cm^2$ $V^{-1}$ $s^{-1}$ using the following equation:

$$g_m = \frac{dI_D}{dV_{GS}} = \frac{W}{L}C_{DL}\mu_{FE}V_D \qquad \text{Eq. No. 1}$$

where W is the channel width, L is the channel length, and $C_{DL}$ is the electrical double layer capacitance per unit area in 0.1 M ionic strength aqueous solution (25.52 μF cm$^{-2}$) (See S. Park, et al, 2015, cited supra). Maximum transconductance 5.69 μS was observed at a drain voltage of 0.2 V and a gate voltage of 0.527 V (FIG. 7). To further confirm the gate control of the on-chip gate electrode, and in accordance with several embodiments, one electrode was used as the gate bias supplier and another as a reference electrode to monitor the actual change of potential on the devices, as the scheme shows in the inset of FIG. 8A. In FIG. 8A, the reference voltage ($V_{REF}$) was plotted against the gold gate voltage ($V_{GS}$) with different distances between those two electrodes, 150 μm, 750 μm, and 1350 μm, respectively. The plot provides that $V_{REF}$ is almost identical to $V_{GS}$ regardless of the distance. Drain current versus gate bias applied through the gold gate at difference distances was also plotted (FIG. 8B), revealing negligible differences between gate-to-channel distances.

A statistical study of key electrical properties for 50 In$_2$O$_3$ nanoribbon devices comparing gate biased through the Ag/AgCl electrode and the gold gate was conducted. FIG. 9 provides that the Ag/AgCl electrode and the gold gate devices performed nearly identically in assays assessing mobility (μ), threshold voltage ($V_{th}$), on/off ration, and on-state current. These data imply that the gold gate and the Ag/AgCl gate can have analogous gating effects. These data provide support that the on-chip gate electrode has a great control over the nanoribbon transistors in the aqueous environment, in accordance with a number of embodiments of the invention.

Flexibility

Figure 10A:
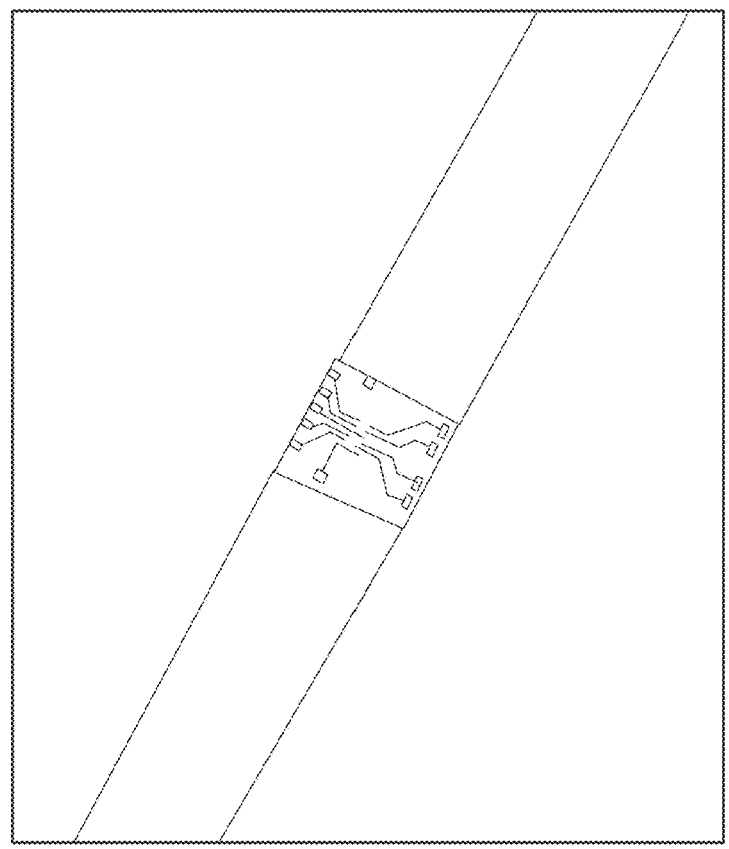
FIG. 10A provides a photograph of a biosensor foil wrapping around a glass cylinder in accordance of various embodiments of the invention. Scale bar is 5 mm.
Figure 10B:
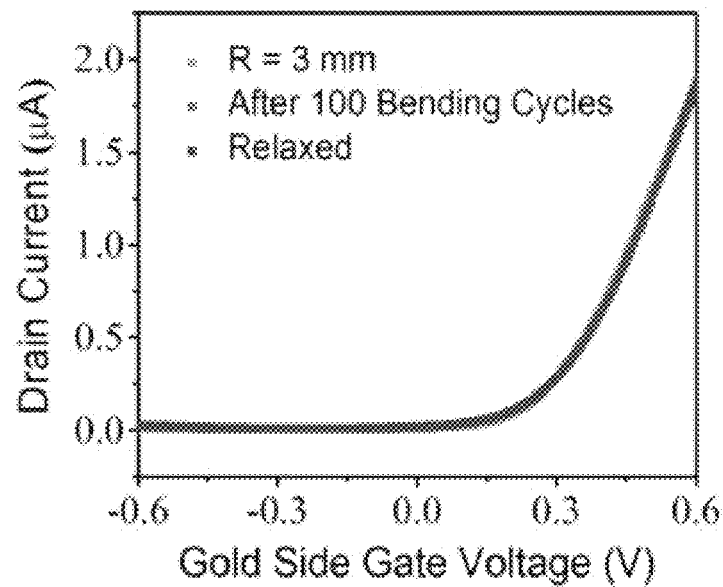
FIG. 10B provides a data plot of transfer characteristics of a representative $In_2O_3$ FET under relaxed state, bent with a radius of ~3 mm, and after bending 100 times, generated in accordance of various embodiments of the invention.

In order to characterize the flexibility of the wearable In$_2$O$_3$ FETs, various bending tests were carried out. As shown in FIG. 10A, fabricated In$_2$O$_3$ foil was tightly wrapped around a cylinder. The electrical performance of the devices under tensile strain was measured. FIG. 10B compares the transfer characteristics of a representative In$_2$O$_3$ nanoribbon FET in three conditions: relaxed status, bent with a radius of curvature of ~3 mm, and after 100 bending cycles. The devices, in accordance with numerous embodiments, exhibited n-type behavior in all three conditions without any perceptible change of their performances. In order to verify the reliability of various devices when deformed, flexibility tests were performed on In$_2$O$_3$ FETs functionalized with a gel film containing chitosan, SWCNT, and glucose oxidase.

Figure 11A:
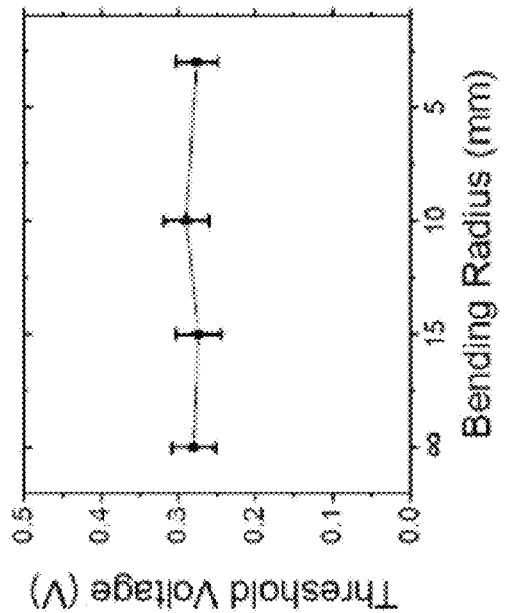
FIGS. 11A, 11B, and 11C provide data graphs detailing mobility, threshold voltage, and on-off ratio of $In_2O_3$ FETs bent with different radii, generated in accordance of various embodiments of the invention.
Figure 11B:
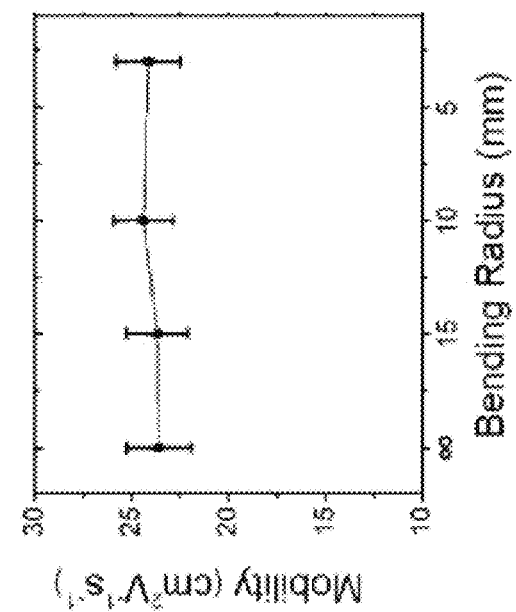
Figure 11C:
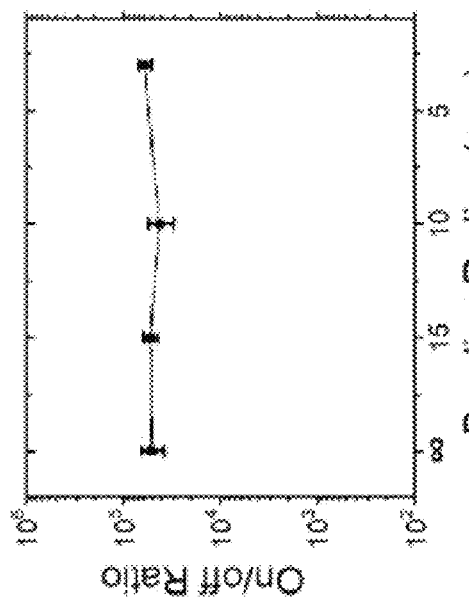
Figure 12A:
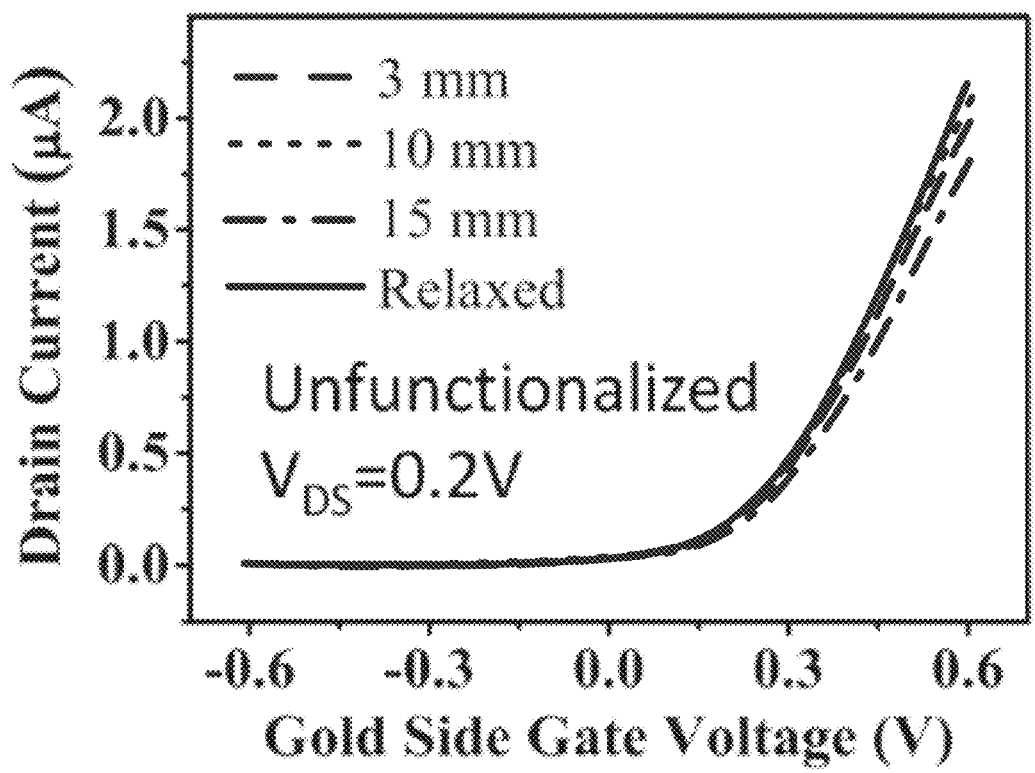
FIGS. 12A and 12B provide data graphs detailing transfer characteristics of unfunctionalized and functionalized $In_2O_3$ FETs under relaxed state, bent with a radius of ~3, 10, and 15 mm, generated in accordance of various embodiments of the invention.
Figure 12B:
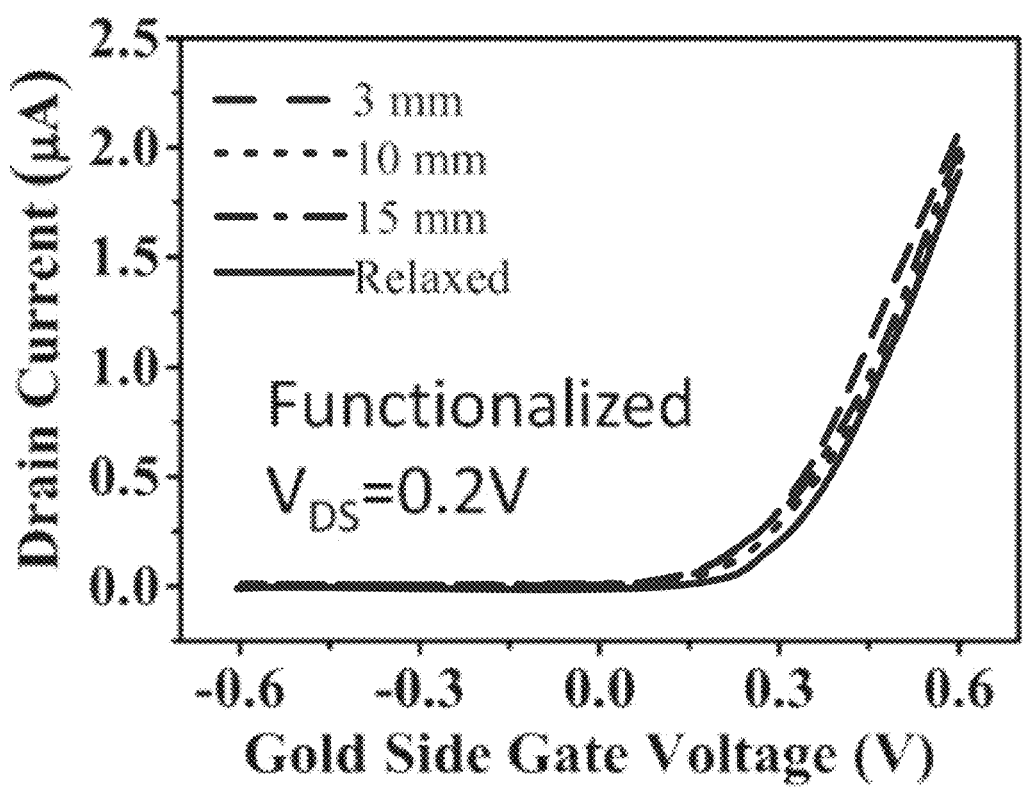

FIG. 11 provides plots of the mobility, the on-off ratio, and the threshold voltage averaged over 9 devices bent with a radius of curvature of infinity (relaxed), 3, 10, and 15 mm, respectively. Exemplary transfer curves of the devices under the different bending conditions are plotted in FIG. 12.

Tensile strain of the various bent In$_2$O$_3$ foils were calculated using the formula:

$$\varepsilon = \frac{1}{R} \times \frac{d_s + d_f}{2} \times \frac{\chi \cdot \gamma^2 + 2 \cdot \chi \cdot \gamma + 1}{\chi \cdot \gamma^2 + \chi \cdot \gamma + \gamma + 1} \qquad \text{Eq. No. 2}$$

where R is the bending radius, $d_s$ is the thickness of the substrate, and $d_f$ is the thickness of In$_2$O$_3$ nanoribbon transistor (TFT). $\gamma = d_f/d_s$ and $\chi = Y_f/Y_s$, where $Y_f$ and $Y_s$ are the Young's modulus of In$_2$O$_3$ FET and the substrate, respectively. Accordingly, $Y_f = Y_s$ is assumed and Eq. No. 2 can be further simplified:

$$\varepsilon = \frac{1}{R} \times \frac{d_s + d_f}{2}$$

Figure 13:
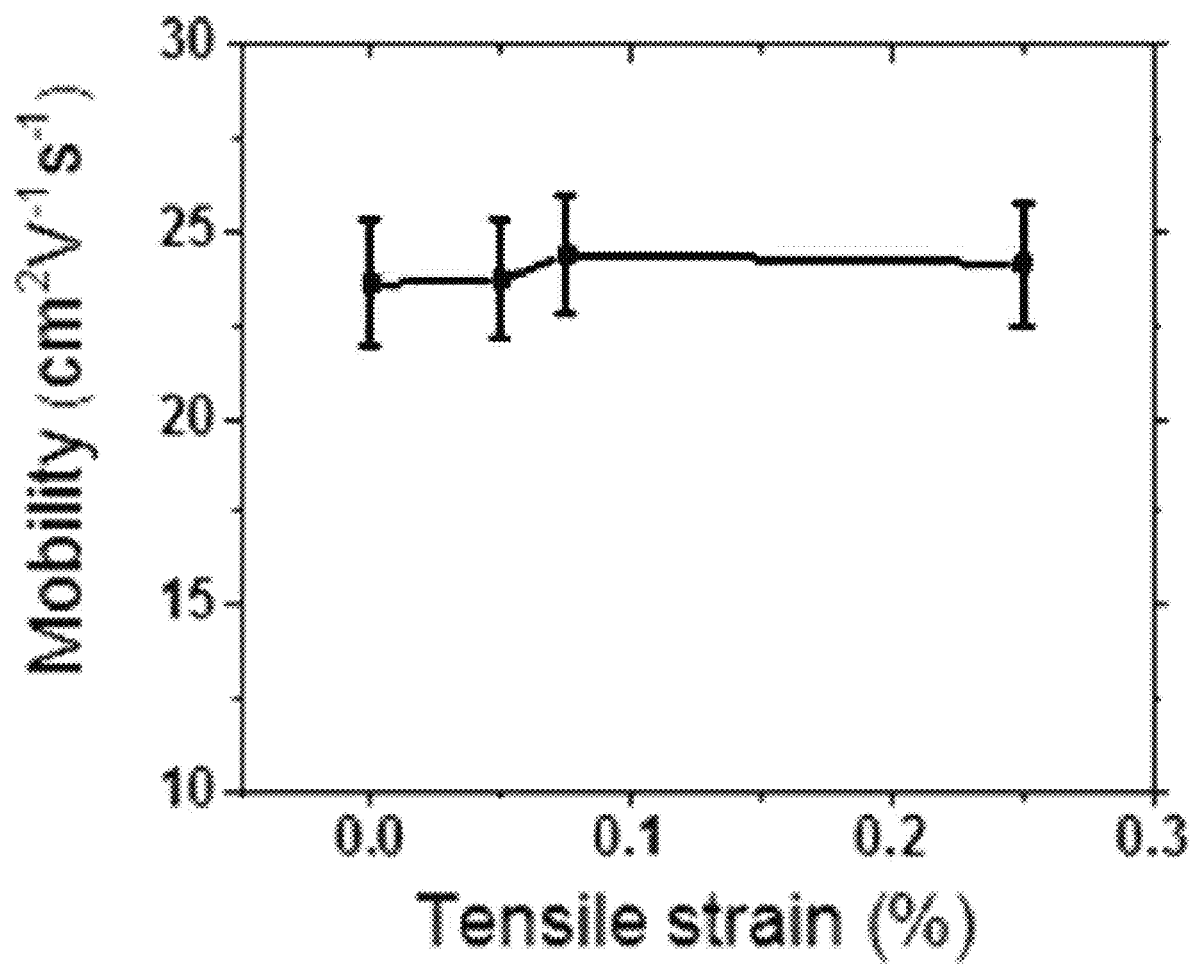
FIG. 13 provides a data graph detailing mobilities of $In_2O_3$ FETs as a function of tensile strain, generated in accordance of various embodiments of the invention.

The thickness of the substrate is 15 μm and the total thickness of the TFT is less than 100 nm. With the bending radius of 3 mm, the tensile strain is calculated to be ~0.25%. The mobility as a function of tensile strain is plotted in FIG. 13.

With a radius of curvature of ~3 mm, a tensile strain of ~0.25%, was applied to In$_2$O$_3$ FETs parallel to the drain-to-source current direction. There was no significant change of the electrical performance of the In$_2$O$_3$ FETs when the devices were in different bending conditions, as the mobility only showed small variation between 22.15±1.68 cm$^2$ V$^{-1}$ s$^{-1}$ and 22.70±1.65 cm$^2$ V$^{-1}$ s$^{-1}$, the threshold voltage only showed variation between 0.273±0.028 V and 0.280±0.027 V, and the logarithm on-off ratio showed variation between 4.71±0.13 and 4.84±0.12.

Figure 14A:
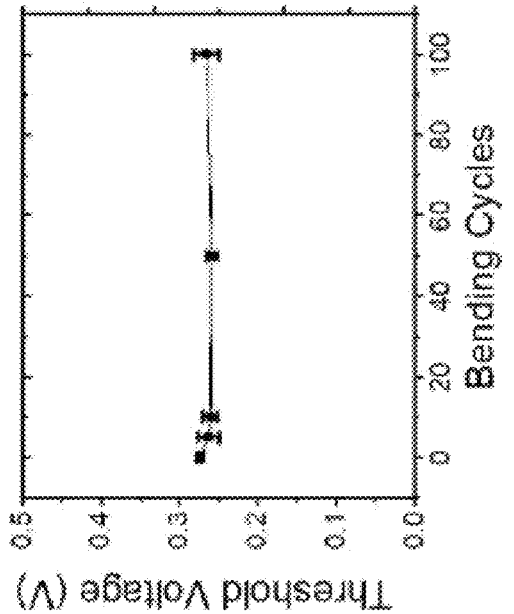
FIGS. 14A, 14B, and 14C provide data graphs detailing mobility, threshold voltage, and on-off ratio of $In_2O_3$ FETs with a radius of ~3 mm after different bending cycles, generated in accordance of various embodiments of the invention.
Figure 14B:
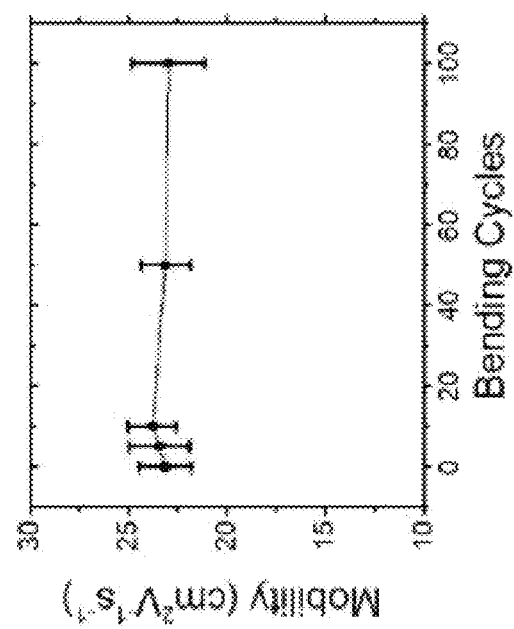
Figure 14C:
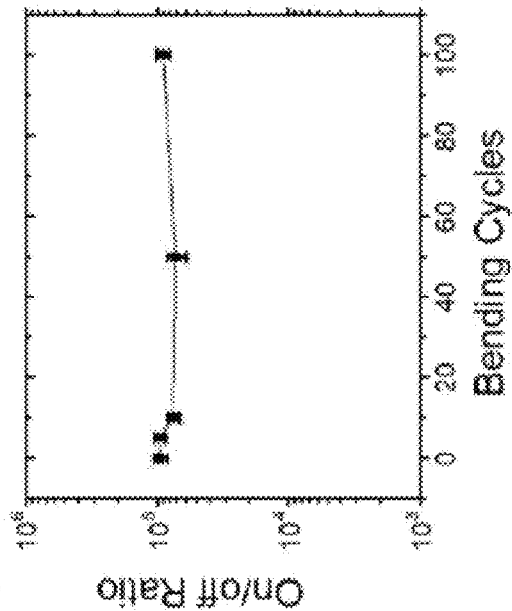
Figure 15A:
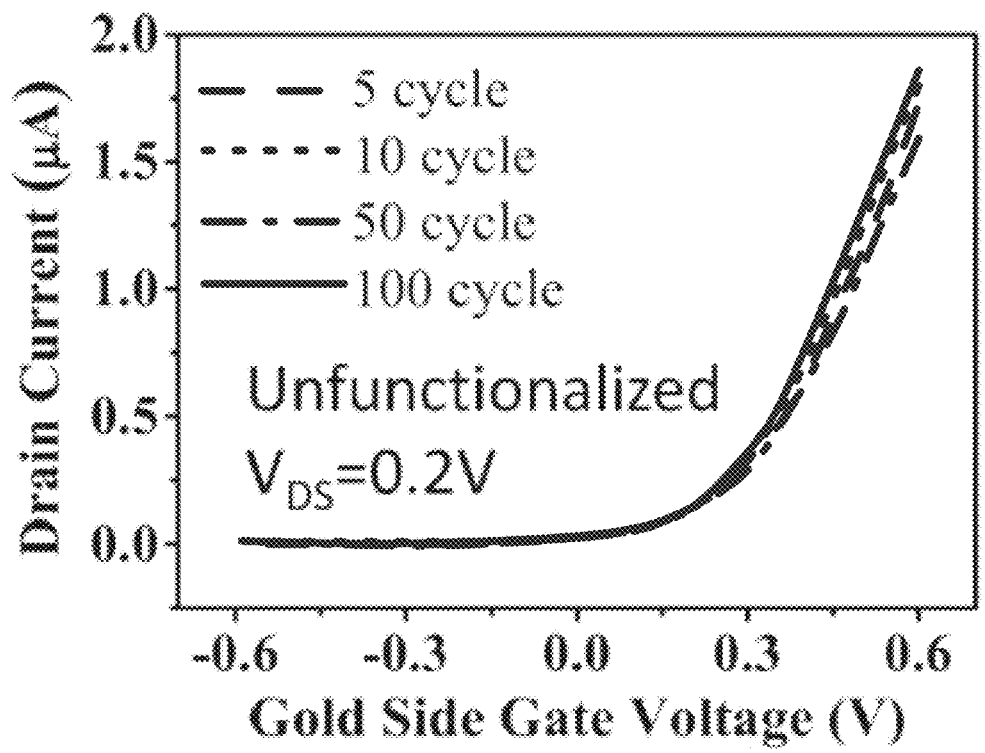
FIGS. 15A and 15B provide data graphs detailing transfer characteristics of unfunctionalized and functionalized $In_2O_3$ FETs after bending with 5, 10, 50, and 100 cycles, generated in accordance of various embodiments of the invention.
Figure 15B:
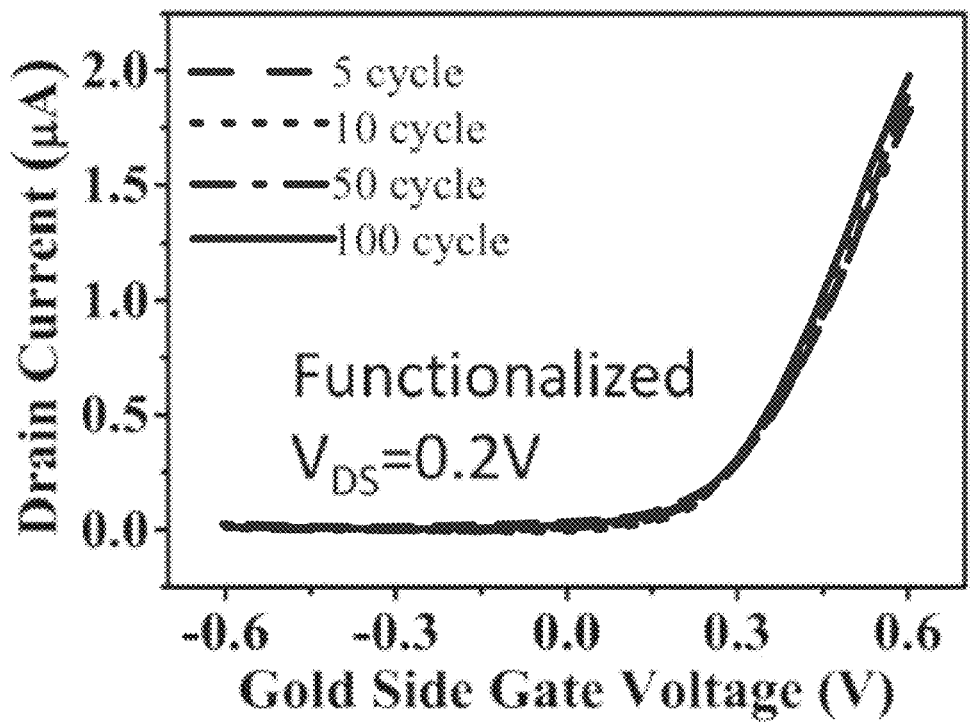

FIG. 14 plots the mobility, the threshold voltage, and the on-off ratio of the devices without bending and after 5, 10, 50, and 100 bending cycles. As can be seen in the figure, the changes in device performance were negligible. The mobility varied in the range of 22.98±1.34 cm$^2$ V$^{-1}$ s$^{-1}$ and 23.78±1.87 cm$^2$ V$^{-1}$ s$^{-1}$, the threshold voltage varied between 0.273±0.005 V and 0.266±0.016 V, and the logarithm on-off ratio varied between 4.98±0.17 to 4.96±0.14. On the basis of the test results, In$_2$O$_3$ nanoribbon FETs after bending tests still maintained excellent performance, confirming that the platform is reliable under mechanical deformation. Exemplary transfer curves of the devices after 5, 10, 50, and 100 bending cycles are plotted in FIG. 15.

pH and Glucose Sensing

Figure 16A:
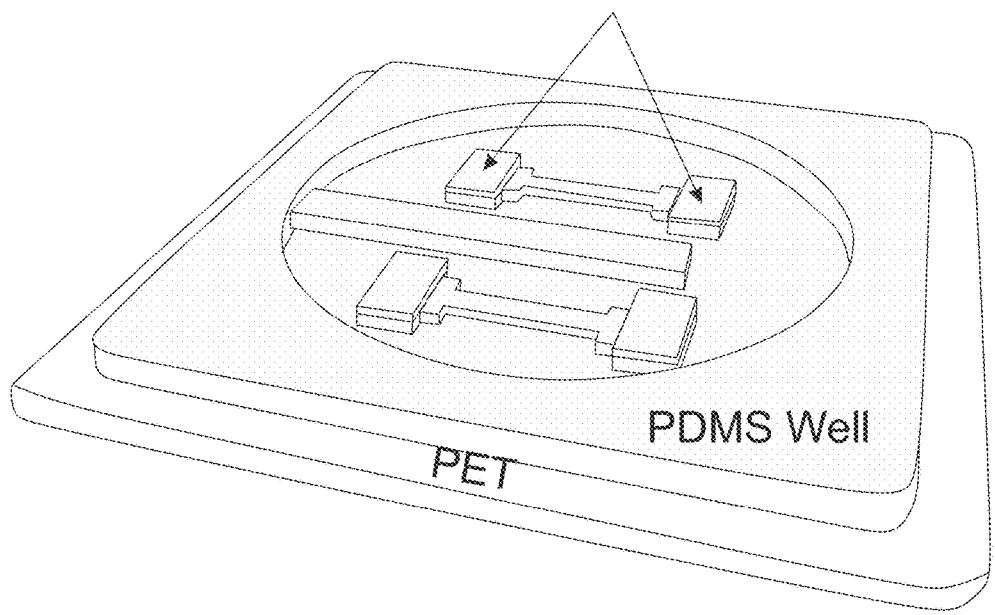
FIG. 16A provides a schematic diagram showing a PDMS microwell is attached to the PET substrate with $In_2O_3$ FETs in accordance of various embodiments of the invention.
Figure 16B:
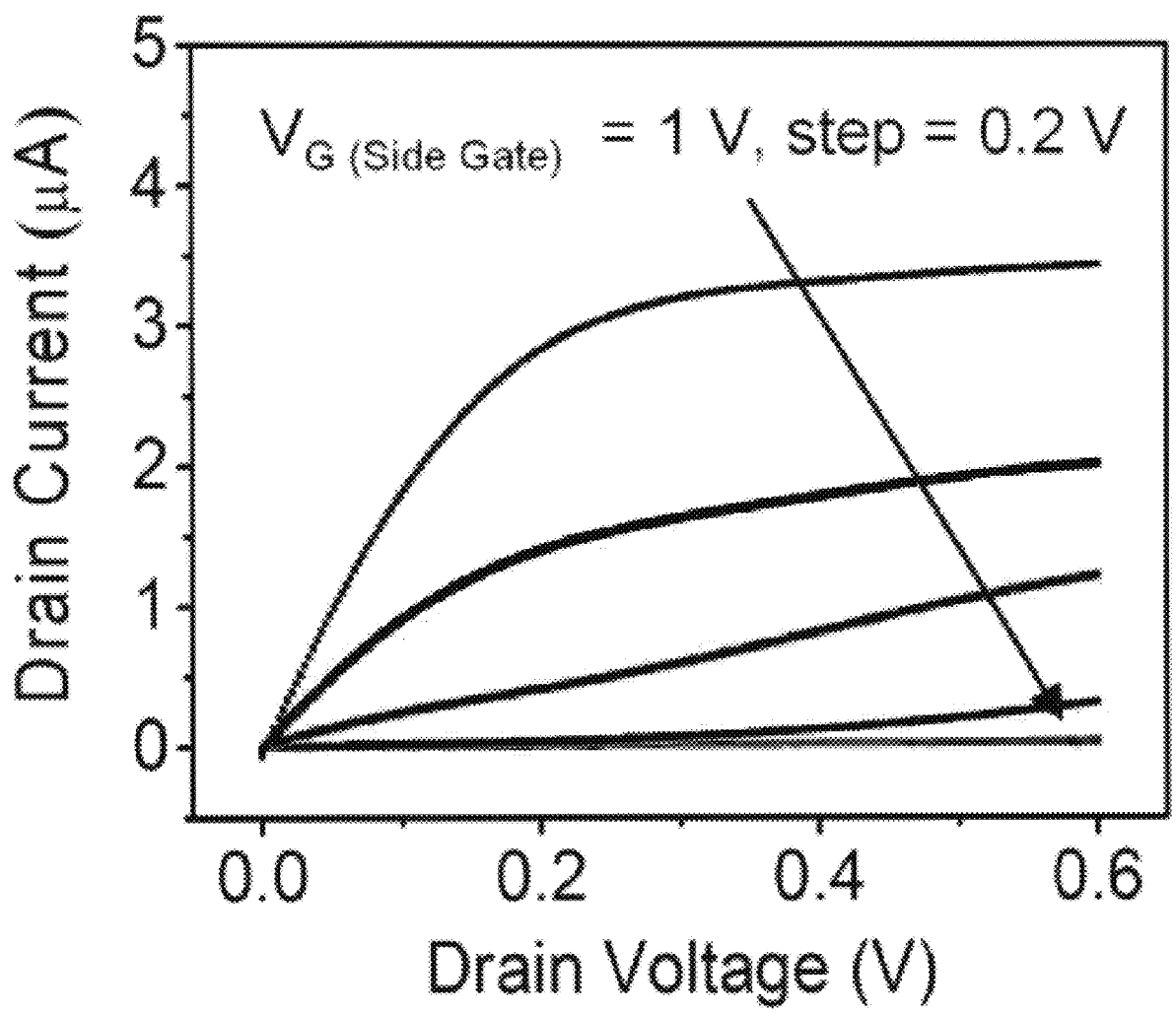
FIG. 16B provides a data graph detailing family curves of $I_{DS}$-$V_{DS}$ measured with the channel area submerged in the PDMS well, generated in accordance of various embodiments of the invention.
Figure 16C:
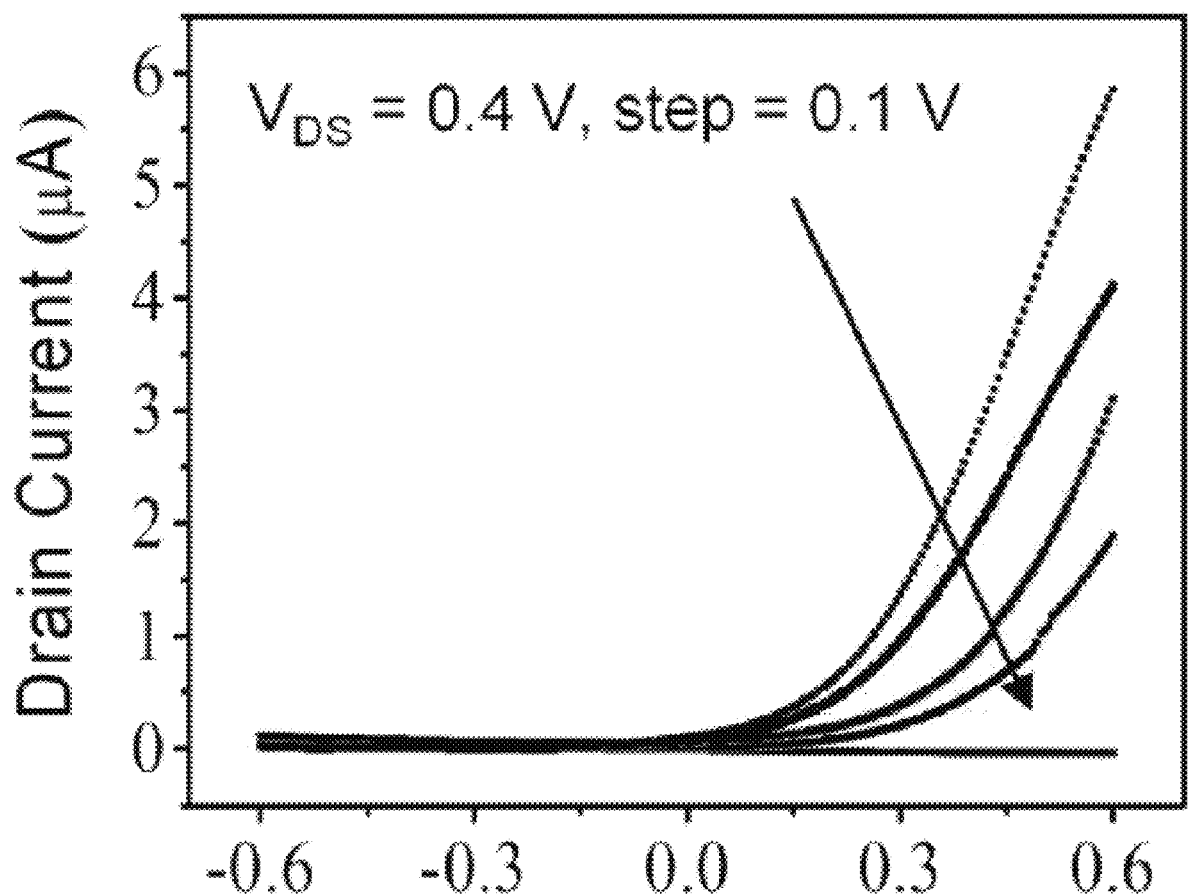
FIG. 16C provides a data graph detailing family curves of $I_{DS}$-$V_{GS}$ measured with the channel area submerged in the PDMS well, generated in accordance of various embodiments of the invention.

Due to low volume of external body fluid, the ability to detect in a small amount of liquid is crucial to wearable sensors. A polydimethylsiloxane (PDMS) stamp was adapted to be used as a microwell to accumulate body fluids (FIG. 16A). It can also serve as a passivation layer to ensure reliable sensing without electrical disturbance that can be introduced by contacting of metal lines with a body and/or body fluids. A mixture of curing agent and PDMS at a ratio of 1:10 was first spin-coated onto a silicon wafer before thermally cured at 80° C. for 1 h. After punching a hole with a diameter of 3 mm, the PDMS stamp was laminated onto the biosensor substrate utilizing van der Waals force. To guarantee the biosensor can work properly in a limited amount of liquid, the PDMS microwell was filled with 10 μL solution and electrical measurements were performed using a gold side gate electrode. FIGS. 16B and 16C provide transfer curves and output curves of the In$_2$O$_3$ FETs measured with a gold gate in the electrolyte of ~10 μL 0.1×PBS, generated in accordance with various embodiments. The electrical performance measured in a small amount of liquid is comparable to the results provide in FIGS. 6C and 6D (measured in 300 μL 0.1×PBS). Accordingly, several embodiments of the described biosensing platforms can efficiently work in the liquid with amount as small as 10 μL, which is a 30-fold decrease from that previous reports (Q. Liu, et al., 2016, cited supra).

Figure 16D:
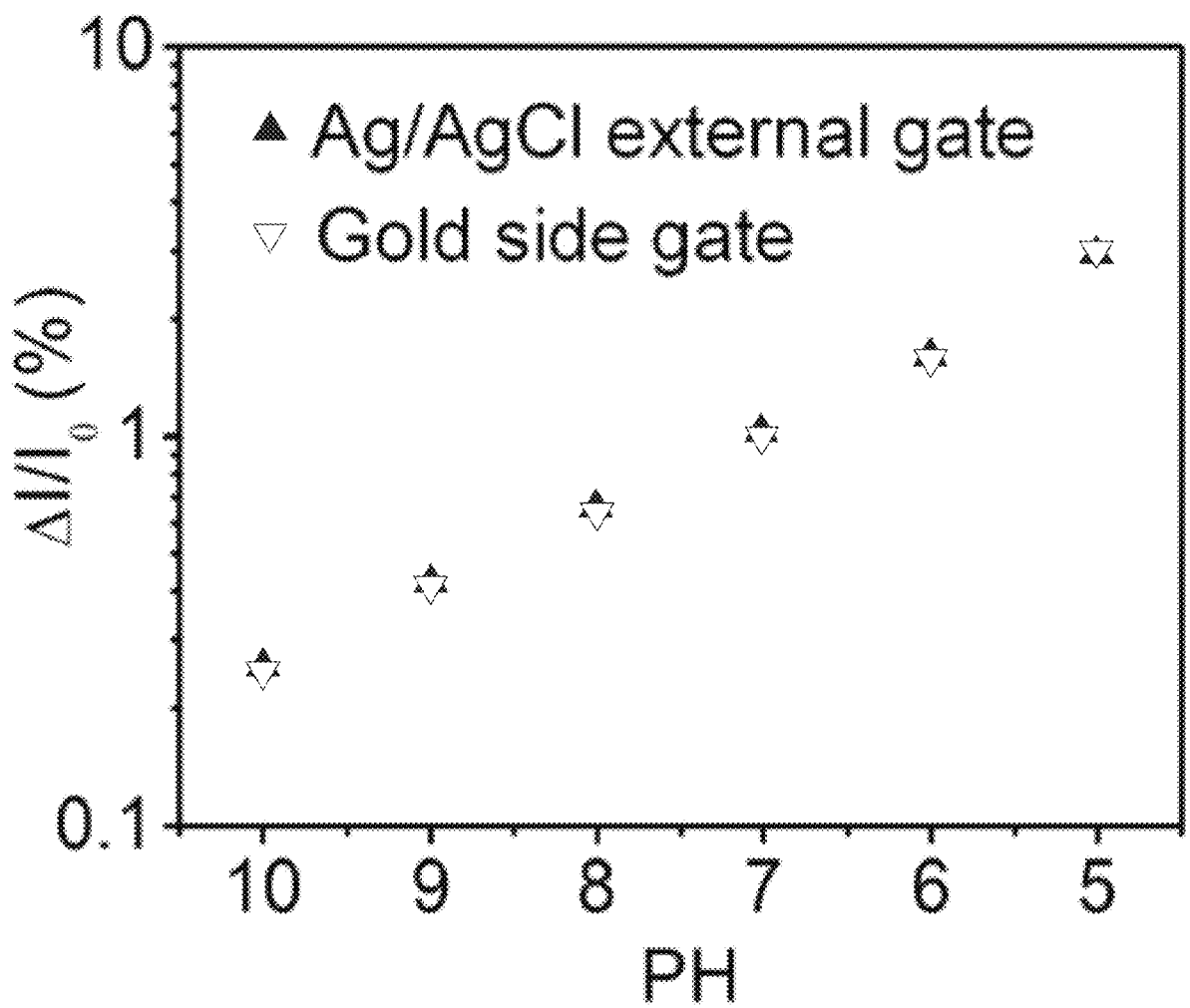
FIG. 16D provides a data graph detailing pH sensing when the gate bias was applied with a Ag/AgCl electrode or a gold side gate electrode, generated in accordance of various embodiments of the invention.
Figure 17A:
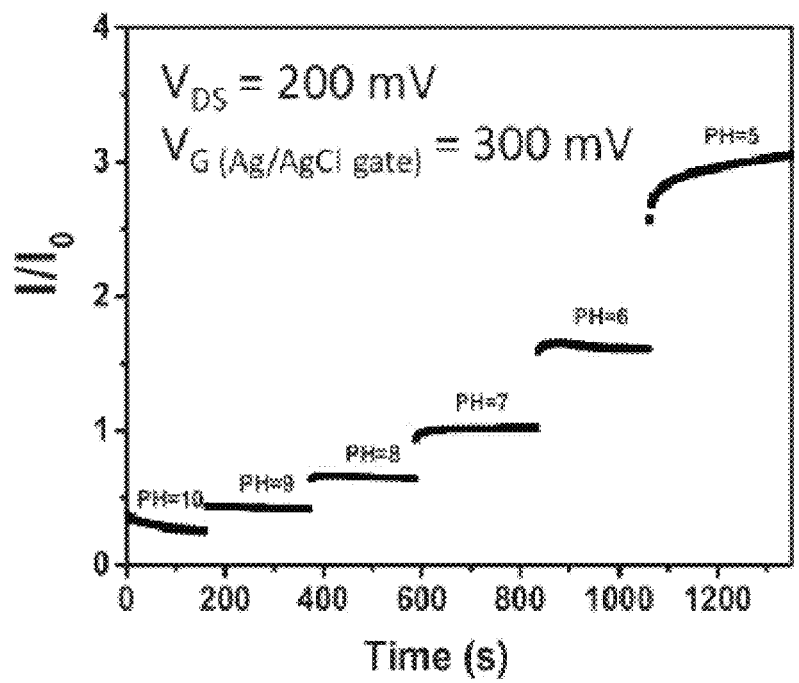
FIGS. 17A and 17B provide data graphs detailing real-time sensing responses of an $In_2O_3$ FET to standard pH calibration solutions, generated in accordance of various embodiments of the invention. Gate voltage is applied with a Ag/AgCl gate electrode, and a gold side gate electrode.
Figure 17B:
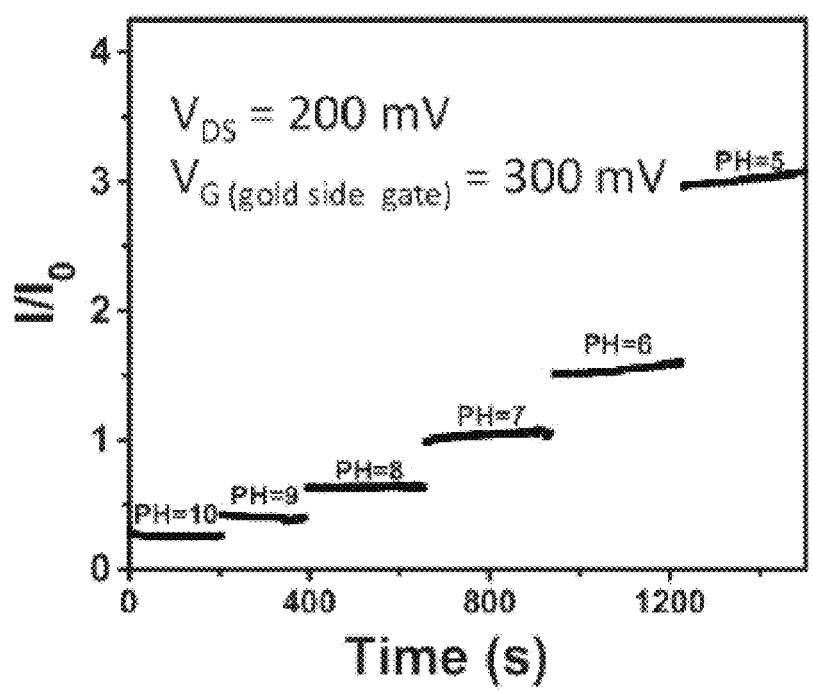

To further establish the sensing ability of the described biosensor platforms, pH sensing experiments were conducted to test the ionic sensitivity of biosensor chips in response to commercial pH solutions. FIG. 16D provides a comparison of the pH sensing responses ($\Delta I/I_0$) with gate bias supplied using either a gold electrodes, in accordance with embodiments, or Ag/AgCl electrodes. The responses are plotted into black upward pointing triangles and red downward pointing triangles for devices gated with a Ag/AgCl external liquid electrode and a gold electrode, respectively. The baseline current $I_0$ was obtained using 0.1×PBS (pH=7.4) to stabilize the device, and then the PBS was sequentially changed to commercial pH buffer solutions ranging from pH 10 to pH 5. Both gold and Ag/AgCl electrode devices increased in conduction when the pH value of the solution decreased, as hydroxyl groups on the nanoribbon surface were protonated due to more $H^+$ ions in the solution, resulting in the positive gating effect on the channel area of the n-type $In_2O_3$ nanoribbon transistor. As observed, the sensing results from the gold and Ag/AgCl gate electrodes are almost identical. They both are exponentially dependent on pH changes, and the drain current increased ~2.4 times when the pH value increased by 1. Representative real-time pH sensing results are provided in FIG. 17.

Figure 18A:
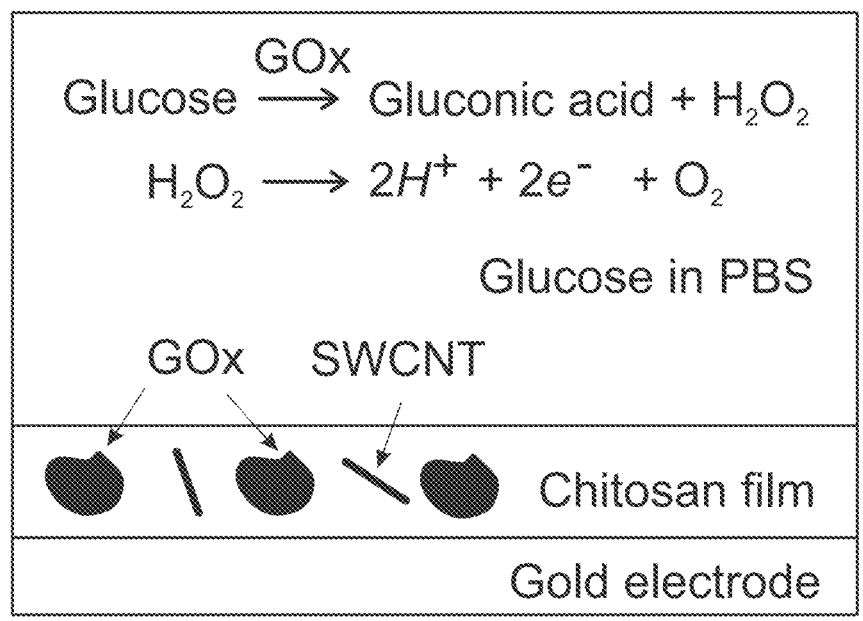
FIG. 18A provides a schematic diagram showing the working principle of glucose sensor in accordance of various embodiments of the invention.

$In_2O_3$ nanoribbon biosensors were also tested for their ability to detect D-glucose. FIG. 18A provides a schematic diagram depicting the working principle of the glucose determination using $In_2O_3$ nanoribbon biosensors, in accordance with various embodiments. The surfaces of source and drain electrodes are functionalized with chitosan/carbon nanotube/glucose oxidase, which can be performed using ink-jet printing. In some embodiments, chitosan is the immobilization layer, which may be beneficial because it is a biocompatible polymeric matrix with good film-forming ability and high water permeability (H. Tang, et al, 2011, cited supra). Carbon nanotubes have been reported as efficient routes for increasing the sensitivity for many types of sensors, owing to their good electrocatalytic property and capacity for biomolecule immobilization (H. Tang, et al, 2011, cited supra; and S. Hrapovic, et al., *Anal. Chem.* 2004, 76, 1083-1088; and J. Wang, M. Musameh, and Y. Lin *J. Am. Chem. Soc.* 2003, 125, 2408-2409, the disclosures of which are herein incorporated by reference). After immobilized onto the chitosan film and carbon nanotubes, glucose oxidase can accept electrons when interacting with glucose in the solution. The accepted electrons thereafter transfer to molecular oxygen to produce hydrogen peroxide ($H_2O_2$), which will be oxidized under a bias voltage. The reactions are as follows:

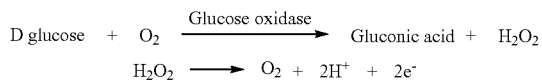

Figure 18B:
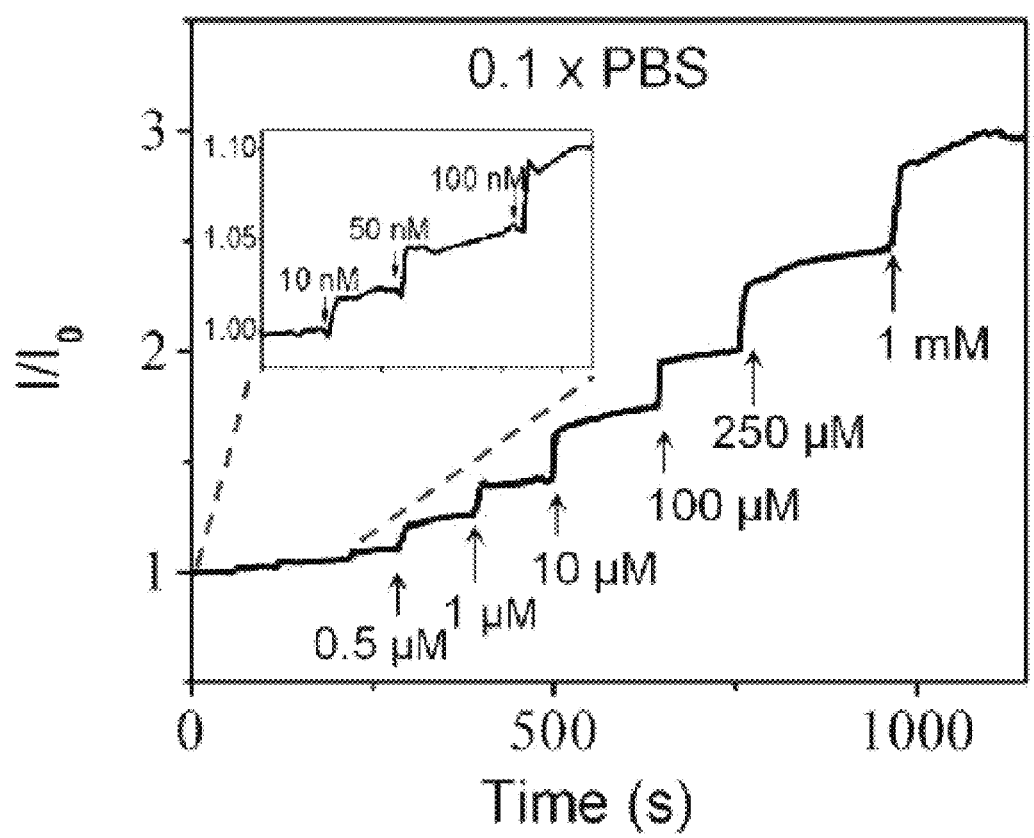
FIG. 18B provide a data graph detailing glucose sensing results in 0.1×PBS with a gold side gate, generated in accordance of various embodiments of the invention.
Figure 19:
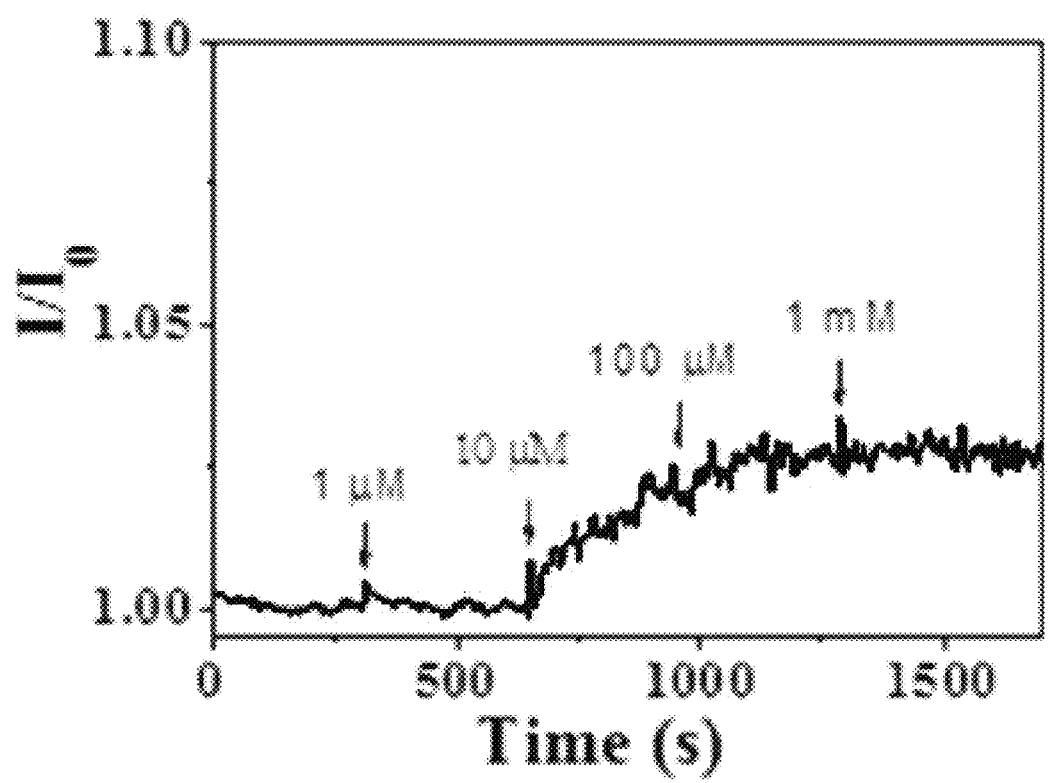
FIG. 19 provides a data graph detailing glucose sensing results of an $In_2O_3$ nanoribbon biosensor functionalized with chitosan and SWCNT only, generated in accordance with various embodiments of the invention.

The generation of $H^+$ depends on the concentration of glucose. Decreasing of the pH leads to protonation the OH groups on the $In_2O_3$ surface and results in changes in the local FET electric field, and ultimately causes changes in the conductance and current. FIG. 18B provides a plot detailing continuous monitoring of sensing signals in response to increasing glucose concentrations. The channel current increases as the concentration of glucose increases, with a detection limit of about 10 nM (~2.2% of the baseline current), in accordance with a number of embodiments. Accordingly, embodiments of glucose sensors can detect glucose in the concentration range between 10 nM to 1 mM, which covers typical glucose concentrations in human body fluids, such as, for example, sweat diabetes patients and healthy people (P. Makaram, D. Owens, and J. Aceros, 2014, cited supra). The detection limit observed with the described embodiments of $In_2O_3$ nanoribbon biosensors is much lower than a typical electrochemical amperometric glucose sensor (W. Gao, et al., 2016, cited supra; and H. Lee, et al., 2017, cited supra). Fabricated sensors merely lacking glucose oxidase did not respond to glucose (FIG. 19).

Wearable $In_2O_3$ nanoribbon glucose sensors are further analyzed in external human body fluid, such as tears, sweat and saliva, which have much lower glucose concentrations than blood. While normal blood glucose levels range between 70 mg/dL (3.9 mM) and 140 mg/dL (7.8 mM) or higher, by contrast, tear glucose levels are on the order of 0.1-0.6 mM (E. R. Berman, BIOCHEMISTRY OF THE EYE, Springer Science & Business Media: 2013; H. Yao, et al., *Biosens. Bioelectron.* 2011, 26, 3290-3296; and H. Yao, et al., *J. Micromech. Microeng.* 2012, 22, 075007; the disclosures of which are herein incorporated by reference), sweat glucose has been reported to be 5 to 20 mg/dL (0.277 mM-1.11 mM) (J. Moyer, et al, 2012, cited supra), and saliva glucose concentrations are around 0.51-2.32 mg/dL (28.3 μM-0.129 mM) (P. Abikshyeet, V. Ramesh, and N. Oza *Diabetes Metab. Syndr. Obes.* 2012, 5, 149; W. Zhang, Y. Du, and M. L. Wang, *Sens. Biosens. Res.* 2015, 4, 23-29; and W. Zhang, Y. Du, and M. L. Wang, *Sens. Biosens. Res.* 2015, 4, 96-102; the disclosures of which are herein incorporated by reference). FIG. 20 provides representative current responses to increasing glucose concentrations in artificial human tears, artificial human sweat, and saliva. Initially, wearable $In_2O_3$ nanoribbon devices, in accordance with various embodiments, were submerged in 0.1×PBS to obtain the baseline current (FIG. 20). When the electrolyte was changed from 0.1×PBS to artificial tears at 150 s, the sensing signal bumped up a little bit, due to the pH difference between the fluids. Signal Noise in artificial tears were higher than the results in PBS (compare FIG. 18B and FIG. 20). This increased amount of noise comes derives from the weaker buffer of the artificial tears, resulting in a decrease in the signal-to-noise ratio and affecting detection limit. The relationships between the glucose concentration and the saturated current response from the real-time sensing data in PBS solution, artificial tears, sweat, and saliva were extracted and plotted (FIG. 20). The high correlation between the data with PBS and the data with artificial tears indicates that the detected signals from tears are attributed to mainly glucose and not other nonspecific proteins. In the cases of artificial sweat and saliva, even though the sensing signals are slightly lower than the responses from PBS, which may be due to their different ionic strengths and complex ingredients, the sensors can differentiate the glucose concentration as low as 0.1 μM. This sensitivity is sufficient to detect glucose in both sweat and saliva, in accordance with many embodiments.

Figure 21A:
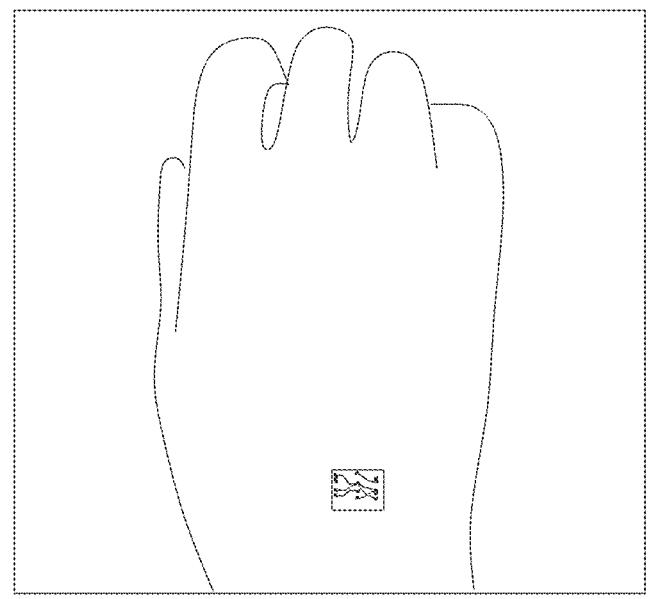
FIGS. 21A and 21B provide photographs of $In_2O_3$ biosensors attached onto an eyeball replica and an artificial arm in accordance with various embodiments of the invention.
Figure 21B:
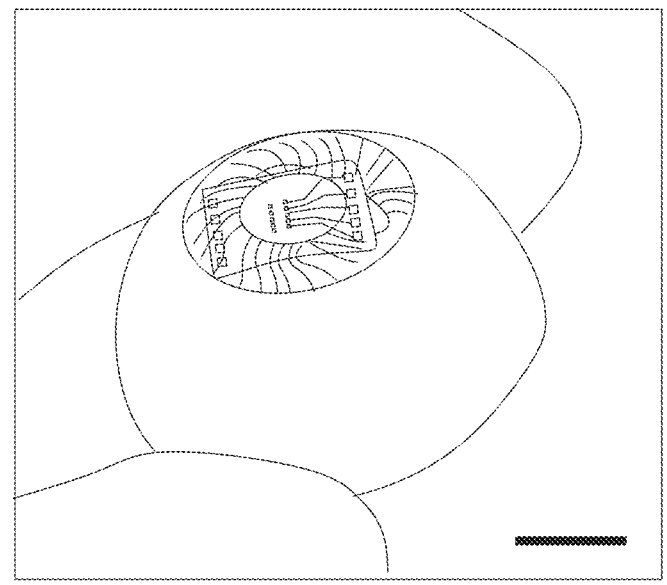
Figure 22A:
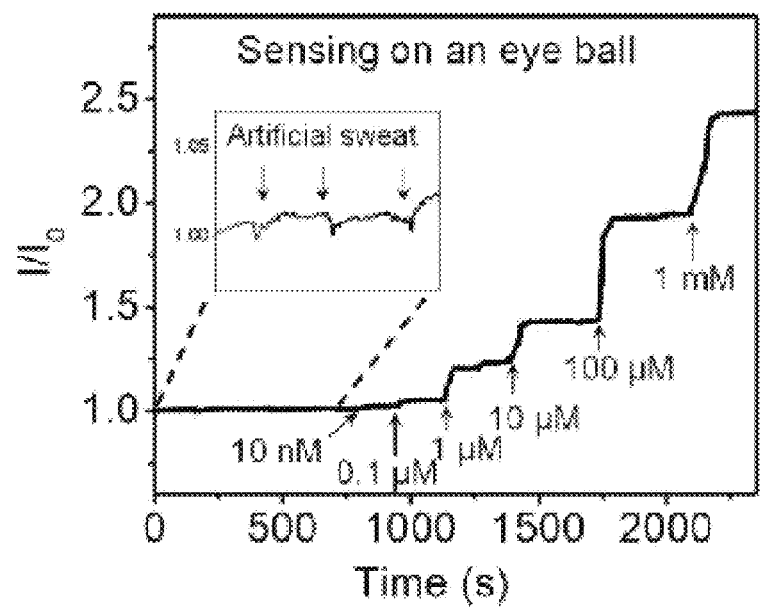
FIGS. 22A and 22B provide data graphs of real-time glucose sensing results on an artificial eyeball and an artificial arm, generated in accordance with various embodiments of the invention.
Figure 22B:
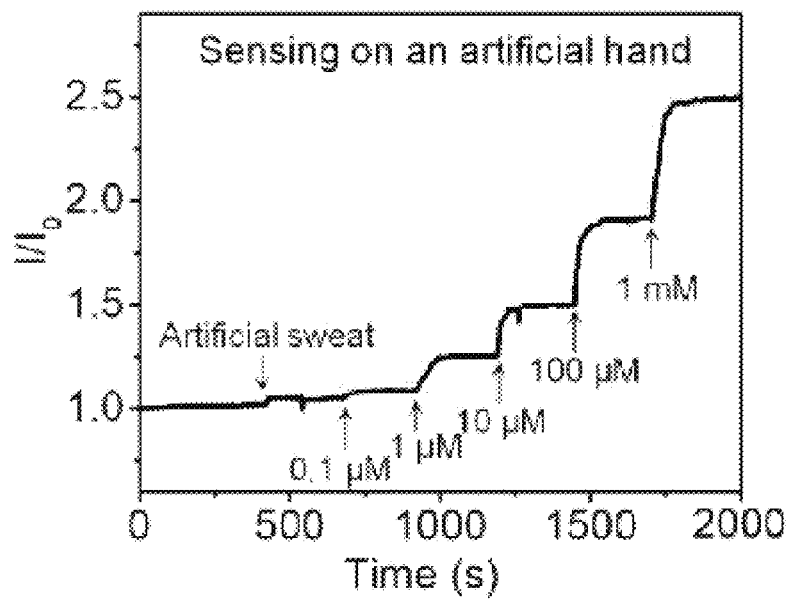

Wearable $In_2O_3$ biosensors, in accordance with multiple embodiments, can be comfortably attached onto an artificial eyeball and an artificial arm (FIG. 21). To ensure the on-body sensing ability, the data collection on an artificial eyeball with the biosensor facing out was imitated. FIG. 22 provides ex-situ glucose sensing results using artificial tears. Indium wires were used to connect the bonding pads to the measurement unit, and artificial tears were constantly flowing through the sensing area (see inset of FIG. 22). After obtaining a stable baseline current, artificial tears were sequentially flowing, spiked with 0.01, 0.1, 1, 10, 100, and 1000 μM glucose. The sensing results demonstrate that the wearable glucose sensing platform, in accordance to several embodiments, can be utilized in conjunction with contact lenses when embedded with various sensors described herein.

Figure 23:
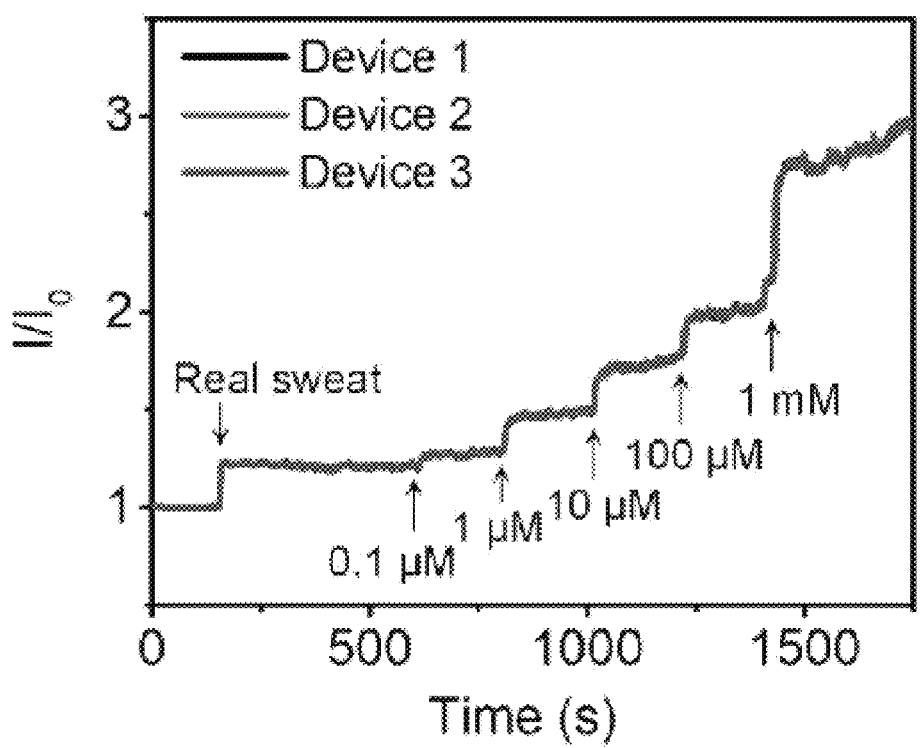
FIG. 23 provides a data graph of real-time glucose sensing with real sweat collected from human subjects, generated in accordance with various embodiments of the invention.

Glucose sensing, according to a number of embodiments, was also performed on an artificial arm, but with the sensor facing the skin. Sensing results are provided in FIG. 22, which demonstrates that $In_2O_3$ biosensors, in accordance with numerous embodiments, can work as sweat patch for glucose monitoring. To further confirm that the sensing platform can be utilized as wearable sweat analyzer, sweat samples was collect from human subjects' foreheads during exercise. The sweat was spiked with different concentrations of glucose and sensing was performed as described herein and in accordance with many embodiments. FIG. 23 provides sensing results with real sweat. The sensing signal shows a large increase after the PBS was replaced with sweat due to the changes in pH and intrinsic glucose concentration. Good sensitivity was observed ranging from 0.1 µM to 1 mM, indicating that the sensing platform described herein can be used for wearable sweat analysis.

Figure 24:
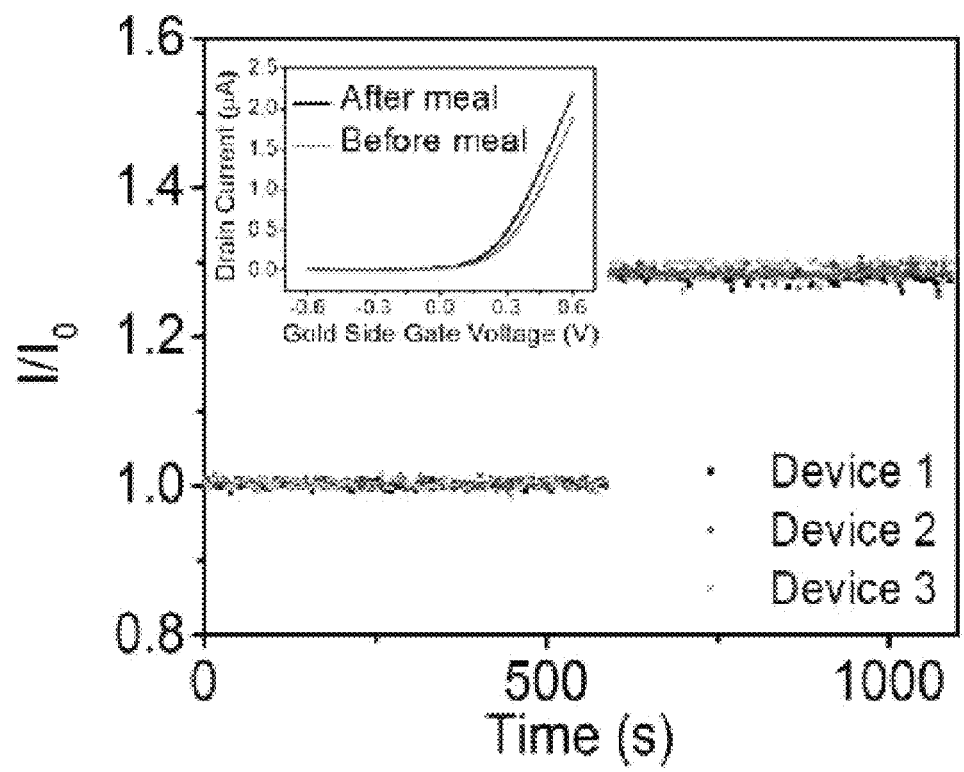
FIG. 24 provides a data graph of glucose sensing results of real sweat collected before and after glucose beverage intake, generated in accordance with various embodiments of the invention.

Sweat glucose levels were also measured before and after meal of an individual with no observable health deficiencies. Sweat samples were collected 30 min before and 30 min after intake of a glucose-rich beverage. The sensing results are provided in FIG. 24. The inset figure provides the device transfer curve measured of sweat samples acquired before and after glucose intake. For comparison, the subject's blood sugar level before and after glucose intake was also recorded using a commercial glucose meter, which recorded glucose concentrations 79 mg/dL and 118 mg/dL, respectively.

Figure 25:
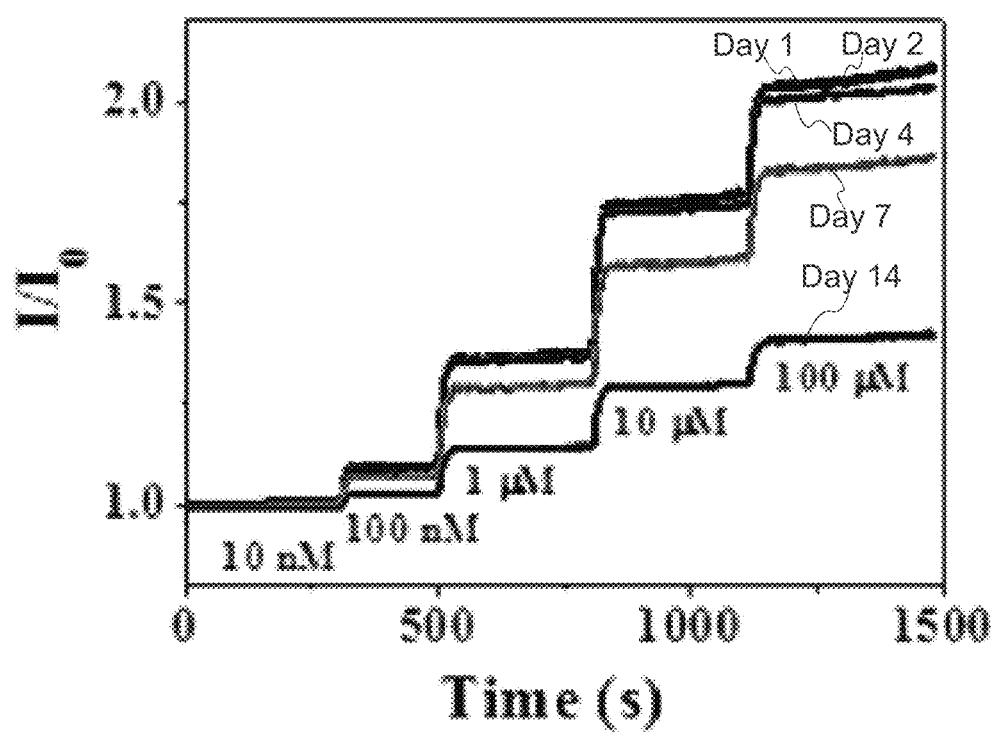
FIG. 25 provides a data graph of glucose sensing results with a functionalized sensor after 1, 2, 4, 7, and 14 days of repeated use, generated in accordance with various embodiments of the invention.

To determine storability of $In_2O_3$ biosensor functionalized with chitosan/CNT/GOx, glucose measurements were performed using a single sensor at intermittent time points over two weeks. The device was used to measure glucose every day and kept stored at 4° C. in between measurements. Results of glucose sensing are provided in FIG. 25. Over the first 4 days, there was little no loss of detected signal. Furthermore, after two weeks, detection of glucose concentrations between 10 µM and 100 µM glucose in PBS decreased only about 25% and 30% (FIG. 25). The decrease in the glucose detection ability can be attributed to the deactivation of the glucose oxidase and/or the loss of enzyme during washing steps. Despite this loss of detection due to repeated uses, it should be noted, that enzyme degradation would be mitigated in a single (or couple) usage regime. Accordingly, embodiments are directed biosensors utilizing low-cost and/or disposable devices, such as devices with $In_2O_3$ FET with gold gate electrodes, as described herein.

Fabrication Process.

A PET substrate was first cleaned with acetone and isopropyl alcohol, and then went through ultra violet treatment before the fabrication process. After the cleaning process, the first shadow mask was attached to the PET substrate to define the channel area. Then the $In_2O_3$ nanoribbons were deposited by RF sputtering (Denton Discovery 550 sputtering system). By simply detaching the shadow mask, well patterned nanoribbons were formed. The source, drain, and gold electrodes were then defined by the second shadow mask, and followed with electron beam evaporation of 1 nm Ti and 50 nm Au. After deposition, the shadow mask was removed.

Characterization Methods.

Optical microscopy images were taken with an Olympus microscope. The SEM images were taken with a Hitachi S-4800 field emission scanning electron microscope. Electrical characteristics and sensing results were measured with an Agilent 1500B semiconductor analyzer.

Device Functionalization.

1 weight % (wt %) chitosan powder was first dissolved in 2 wt % acetic acid aqueous solution. Next, the chitosan solution was mixed with single-walled carbon nanotubes (SWCNT) (2 mg ml$^{-1}$ in 1×PBS) using ultrasonication for over 30 min. The chitosan/SWCNT solution was mixed with glucose oxidase solution (10 mg ml$^{-1}$ in 1×PBS) in the volume ratio 2:1. The mixed solution was then ink-jet printed onto the source and drain electrode, and dried under ambient conditions.

Human Body Fluid Samples.

Artificial human tear was bought from Walgreens. Artificial human sweat was prepared by mixing 22 mM urea, 5.5 mM lactic acid, 3 mM $NH_4^+$, 100 mM $Na^+$, 10 mM $K^+$, 0.4 mM $Ca^{2+}$, 50 µM $Mg^{2+}$ and 25 µM uric acid with varying glucose concentrations. Real sweat samples were collected from human by scratching their foreheads with micro tubes.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention. Accordingly, the scope of the invention should be determined not by the embodiments illustrated, but by the appended claims and their equivalents.

What is claimed is:

1. A biosensor comprising:
    a flexible substrate; and
    at least one field effect transistor assembly comprising a pair of flexible field effect transistors deposited onto the flexible substrate, each pair of flexible field effect transistors including:
        a first electrode assembly including a first source electrode, a first drain electrode, and a first metal oxide channel, the first metal oxide channel contacting the first source electrode and the first drain electrode;
        a second electrode assembly including a second source electrode, a second drain electrode, and a second metal oxide channel, the second metal oxide channel contacting the second source electrode and the second drain electrode; and
        a malleable gate electrode deposited onto the flexible substrate, the malleable gate electrode interposed between the first electrode assembly and the second electrode assembly.

2. The biosensor of claim 1 wherein the first metal oxide channel and the second metal oxide channel each independently comprise an indium oxide.

3. The biosensor of claim 1 wherein the first metal oxide channel includes a first ribbon section having a first length and a first width, the first length being greater than the first width, the first metal oxide channel defining a first axis through the first ribbon section and the second metal oxide channel includes a second ribbon section having a second length and a second width, the second length being greater than the second width, the second metal oxide channel defining a second axis through the second ribbon section.

4. The biosensor of claim 3 wherein the first axis is substantially parallel to the second axis.

5. The biosensor of claim 3 wherein the malleable gate electrode has a rectangular cross-section that defines a third axis that is substantially parallel to the first axis and second axis.

6. The biosensor of claim 1, further comprising glucose oxidase deposited on at least one of the first source electrode, the second source electrode, the first drain electrode, and the second drain electrode.

7. The biosensor of claim 6, further comprising glucose oxidase deposited on each of the first source electrode, the second source electrode, the first drain electrode, and the second drain electrode.

8. The biosensor of claim 6, further comprising chitosan and single-walled carbon nanotubes deposited with the glucose oxidase on at least one of the first source electrode, the second source electrode, the first drain electrode, and the second drain electrode.

9. The biosensor of claim 6, further comprising chitosan and single-walled carbon nanotubes deposited with the glucose oxidase on each of the first source electrode, the second source electrode, the first drain electrode, and the second drain electrode.

10. The biosensor of claim 6, wherein the biosensor is capable of detecting glucose in an external body fluid.

11. The biosensor of claim 10, wherein the external body fluid is a fluid selected from the group consisting of sweat, tears, and saliva.

12. The biosensor of claim 10, wherein the biosensor is able to detect glucose concentrations between 10 nM to 1 mM in a solvent.

13. The biosensor of claim 1, wherein the biosensor is conformable to a human feature.

14. The biosensor of claim 13, wherein the biosensor is conformable to human skin.

15. The biosensor of claim 14, wherein the biosensor is integrated into a skin patch.

16. The biosensor of claim 14, wherein the biosensor is integrated into a watch.

17. The biosensor of claim 13, wherein the biosensor is conformable to a human eye.

18. The biosensor of claim 17, wherein the biosensor is integrated into a contact lens.

19. The biosensor of claim 1 further comprising a third electrode assembly and a fourth electrode assembly flanking the pair of flexible field effect transistors.

20. The biosensor of claim 1, wherein the flexible substrate comprises polyethylene terephthalate (PET).

21. The biosensor of claim 1, wherein the malleable gate electrode comprises gold.

22. The biosensor of claim 1, wherein the first source electrode, the second source electrode, the first drain electrode, and the second drain electrode each independently comprise gold.

23. The biosensor of claim 1 further comprising one or more additional pairs of flexible field effect transistors.

* * * * *